US011826139B2

(12) United States Patent
Jin et al.

(10) Patent No.: US 11,826,139 B2
(45) Date of Patent: Nov. 28, 2023

(54) SYSTEM AND METHOD FOR TRACKING A BODY

(71) Applicant: Carnegie Mellon University, Pittsburgh, PA (US)

(72) Inventors: Haojian Jin, Pittsburgh, PA (US); Zhijian Yang, Champaign, IL (US); Swarun Kumar Suresh Kumar, Pittsburgh, PA (US); Jason I. Hong, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 372 days.

(21) Appl. No.: 16/769,741

(22) PCT Filed: Dec. 7, 2018

(86) PCT No.: PCT/US2018/064470
§ 371 (c)(1),
(2) Date: Jun. 4, 2020

(87) PCT Pub. No.: WO2019/113441
PCT Pub. Date: Jun. 13, 2019

(65) Prior Publication Data
US 2020/0375497 A1    Dec. 3, 2020

Related U.S. Application Data

(60) Provisional application No. 62/708,412, filed on Dec. 8, 2017.

(51) Int. Cl.
*A61B 5/107*    (2006.01)
*A61B 5/11*    (2006.01)
(Continued)

(52) U.S. Cl.
CPC .......... *A61B 5/1071* (2013.01); *A61B 5/1114* (2013.01); *A61B 5/1126* (2013.01);
(Continued)

(58) Field of Classification Search
CPC ... A61B 5/1071; A61B 5/1114; A61B 5/1126; A61B 5/6804; A61B 2562/046;
(Continued)

(56) References Cited

U.S. PATENT DOCUMENTS 9,564,682 B2     2/2017   Rhoads et al.
2006/0232407 A1  10/2006  Ballard
(Continued)

OTHER PUBLICATIONS

Adib et al., "3D Tracking via Body Radio Reflections", 13 pages.
(Continued)

*Primary Examiner* — Patrick Fernandes
*Assistant Examiner* — Joseph A Tombers
(74) *Attorney, Agent, or Firm* — THE WEBB LAW FIRM

(57) ABSTRACT

Provided is a system, method, and apparatus for tracking a body. The method includes communicating at least one activation signal to each RF transponder of a first array and a second array, receiving a plurality of response signals from the first array and the second array, the plurality of response signals comprising a response signal for each RF transponder of the first array and the second array, determining a difference in distances between the antenna and each RF transponder of the first array and each transponder of the second array based at least partially on at least one corresponding response signal of the plurality of response signals, and determining a relative location of the first portion of the body and the second portion of the body.

28 Claims, 18 Drawing Sheets

(51) Int. Cl.
*A61B 5/00* (2006.01)
*G01S 13/72* (2006.01)
*H01Q 1/27* (2006.01)
*H04B 1/59* (2006.01)

(52) U.S. Cl.
CPC ............ *A61B 5/6804* (2013.01); *G01S 13/72* (2013.01); *H01Q 1/273* (2013.01); *H04B 1/59* (2013.01); *A61B 2562/046* (2013.01)

(58) Field of Classification Search
CPC . A61B 5/1128; A61B 2562/0257; A61B 5/00; G01S 13/72; H01Q 1/273; H04B 1/59
See application file for complete search history.

(56) References Cited

U.S. PATENT DOCUMENTS

| | | | |
|---|---|---|---|
| 2009/0174529 A1* | 7/2009 | Hertwig | H04B 1/59 340/10.5 |
| 2010/0201512 A1 | 8/2010 | Stirling et al. | |
| 2011/0148607 A1 | 6/2011 | Zeleny | |
| 2013/0289382 A1 | 10/2013 | Rofougaran et al. | |
| 2014/0266935 A1* | 9/2014 | Tankiewicz | H01Q 7/06 343/720 |
| 2016/0000374 A1* | 1/2016 | Dandekar | A61B 90/98 600/587 |
| 2017/0014049 A1 | 1/2017 | Dumanyan et al. | |
| 2017/0188980 A1* | 7/2017 | Ash | A61B 5/744 |

OTHER PUBLICATIONS

Daponte et al., "Electronic Measurements in Rehabilitation", IEEE on Medical Measurements and Applications Proceedings, 2011, 6 pages.
Ding et al., "FEMO: A Platform for Free-weight Exercise Monitoring with RFIDs", Proceedings of the 13th ACM Conference on Embedded Networked Sensor Systems, Nov. 2015, pp. 141-154.
Jin et al., "Towards Wearable Everyday Body-Frame Tracing using Passive RFIDs", Proc. ACM Interact. Mob. Wearable Ubiquitous Technol. 9, 4, Article 1, Sep. 2017, pp. 1-23.
Kellomaki et al., "Towards Washable Wearable Antennas: A Comparison of Coating Materials for Screen-Printed Textile-Based UHF RFID Tags", International Journal of Antennas and Propagation, 2012, 11 pages, Hindawi Publishing Corporation.
Kim et al., "Wearable UHF RFID Tag Antenna Design Using Flexible Electro-Thread and Textile", Antennas and Propagation Society International Symposium, IEEE, 2007 pp. 5487-5490.
Kim et al., "Design of a UHF RFID Fiber Tag Antenna with Electric-thread using a Sewing Machine", Microwave Conference, IEEE, 2008, 4 pages.
Li et al., "Human Sensing Using Visible Light Communication", Proceedings on the 21st Annual International Conference on Mobile Computer and Networking, 2015, pp. 331-344.
Li et al., "IDSense: A Human Object Interaction Detection System Based on Passive UHF RFID", Proceedings of the 33rd Annual ACM Conference on Human Factors in Computing Systems, 2015, pp. 2555-2564.
Ohsawa et al., "Smart-Furoshiiki: A Sensorized Fabrics Supporting Office Activities", UbiComp '06: Proceedings of the 8th International Conference on Ubiquitous Computing, 2006, vol. 9, 2 pages.
Poupyrev et al., "Project Jacquard: Interactive Digital Textiles at Scale", Proceedings of the 2016 CHI Conference on Human Factors in Computer Systems, 2016, pp. 4216-4227.
Schmidt, "Multiple Emitter Location and Signal Parameter Estimation", IEEE Transactions on Antennas and Propagation, Mar. 1986, vol. AP34, No. 3, pp. 275-280.
Spielberg et al., "RapID: A Framework for Fabricating Low-Latency Interactive Objects with RFID Tags", Proceedings of the CHI Conference on Human Factors in Computer Systems, 2016, 12 pages.
Wang et al., "RF-IDraw: virtual touch screen in the air using RF signals", SIGCOMM, 2014, 13 pages, Association for Computing Machinery.
Wang et al., "Towards Washable Electrotextile UHF RFID Tags: Reliability Study of Epoxy-Coated Copper Fabric Antennas", International Journal of Antennas and Propagation, vol. 2015, Article ID 424150, 8 pages, Hindawi Publishing Corporation.
Wei et al., "Gyro in the Air: Tracking 3D Orientation of Batteryless Internet-of-Things", Proceedings of the 22nd Annual Conference on Mobile Computer and Networking, 2016, pp. 55-67.
Xiong et al., "ArrayTrack: A Fine-Grained Indoor Location System", NSDI '13, 2013, pp. 71-84.
Yang et al., "Tagoram: Real-Time Tracing of Mobile RFID Tags to High Precision Using COTS Devices", Proceedings of the 20th Annual International Conference on Mobile Computing and Networking, 2014, pp. 237-248.
Yao et al., "bioLogic: Natto Cells as Nanoactuators for Shape Changing Interfaces", CHI 2015, pp. 1-10.

* cited by examiner

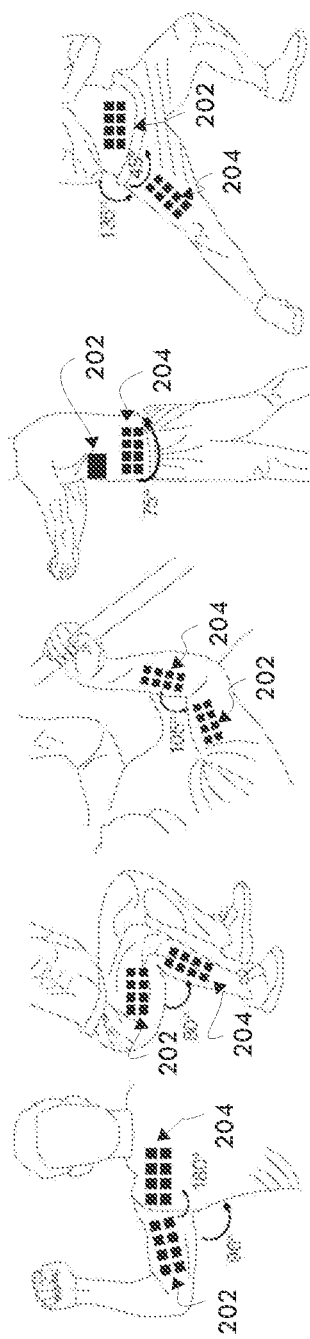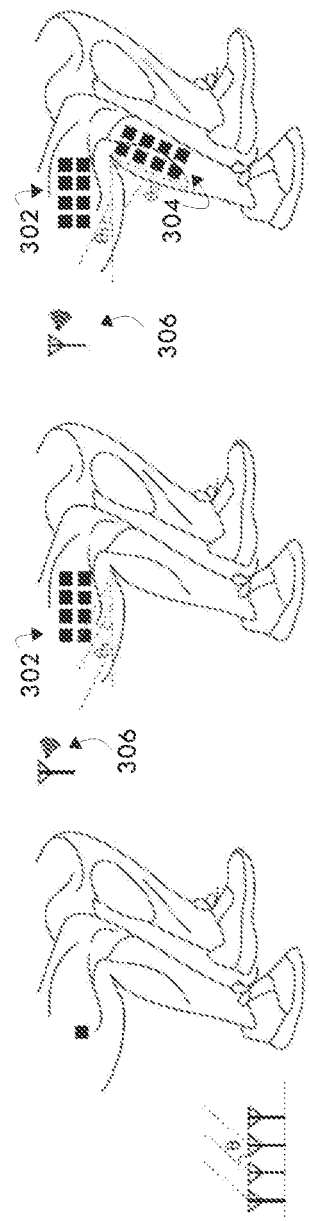

SYSTEM AND METHOD FOR TRACKING A BODY

CROSS-REFERENCE TO RELATED APPLICATIONS

This application is the United States national phase International Application No. PCT/US2018/064470 filed Dec. 7, 2018, and claims priority to U.S. Provisional Patent Application No. 62/708,412, filed Dec. 8, 2017, the disclosures of which are hereby incorporated by reference in their entirety.

GOVERNMENT LICENSE RIGHTS

This invention was made with Government support under CNS-1718435 awarded by the Natural Science Foundation. The Government has certain rights in the invention.

BACKGROUND

1. Field

This disclosure relates generally to body tracking and, in non-limiting embodiments, systems and methods for tracking movement and/or relative location of one or more body parts.

2. Technical Considerations

Many of today's wearable devices can measure the movement of body parts they are attached to, but are not convenient or usable to track movements of all parts of a user's body as they carry on with their daily activities.

Virtual or augmented reality headsets are usually unaware of the current position of a user's body or what gestures are being made by the user. Instead, users of such headsets look downward to see a body of a character that does not match their own body's positioning or movement.

Infrastructure-based solutions, such as the Microsoft Kinect®, or LED-based and RF-based solutions, can perform accurate body-frame tracking but operate only in environments where a specific infrastructure is deployed. Existing RF-based solutions require multiple reader antennas arranged to position transponders through triangulation or tri-lateration, thereby requiring a complicated arrangement of readers and transponders and being unusable with mobile or handheld systems. Existing systems also require calibration during configuration.

Some approaches to body tracking involve directly measuring the angles at a user's joints to track posture. For example, an existing wearable system called the sensor jacket measures the wearer's upper body posture utilizing eleven knitted stretch sensors placed over the joints. Another example is SensorTape®, which deploys a dense lightweight inertial sensor network on tapes to track the tape curvature. Most existing wearable tracking systems are designed to be used in specific contexts where the added bulk and cost are not pertinent, such as therapy, sports training, and three-dimensional movie making. These existing systems also require batteries and heavy electronics to be worn which add to the bulkiness of the system, restrict movements, compromise the tracking accuracy, and are not machine washable. Such systems are not intended for day-to-day use beyond these specific contexts.

Some systems have been developed to detect gestures using smart fabrics. For example, Project Jacquard uses conductive yarns to weave touch and gesture-sensitive areas into a textile, but such sensing is limited to touch. Biologic takes advantage of the hygromorphic phenomenon in living cells to build electronics-free fabric material, but such sensing capability is restricted to humidity.

SUMMARY

According to a non-limiting embodiment, provided is a method for tracking a body comprising a plurality of arrays of radio frequency (RF) transponders arranged thereon, the plurality of arrays comprising a first array of RF transponders arranged on a first portion of the body and a second array of RF transponders arranged on a second portion of the body, the first portion of the body and the second portion of the body connecting at a first joint of the body, the method including: communicating, with an antenna of a reader device, at least one activation signal to each RF transponder of the first array and the second array; receiving, with the antenna, a plurality of response signals from the first array and the second array, the plurality of response signals comprising a response signal for each RF transponder of the first array and the second array; determining, with at least one processor, a difference in distances between the antenna and at least two RF transponders of the first array and a difference in distances between the antenna and at least two RF transponders of the second array based at least partially on at least a portion of the plurality of response signals; and determining, with at least one processor, a relative location of the first portion of the body and the second portion of the body based at least partially on the difference in distances between the antenna and the at least two RF transponders of the first array, a distance between the at least two RF transponders of the first array, the difference in distances between the antenna and the at least two RF transponders of the second array, and a distance between the at least two RF transponders of the second array.

In non-limiting embodiments, the difference in distances between the antenna and the at least two RF transponders of the first array and the at least two RF transponders of the second array are determined based on phases of the at least a portion of the plurality of response signals. In non-limiting embodiments, the plurality of arrays of RF transponders further comprise a third array of RF transponders arranged on a third portion of the body and a fourth array of RF transponders arranged on a fourth portion of the body, wherein the third portion of the body and the fourth portion of the body connect at a second joint of the body. In non-limiting embodiments, the plurality of arrays of RF transponders are integrated into a fabric material adapted to be worn on the body. In non-limiting embodiments, the reader device is arranged on the body and comprises the at least one processor.

In non-limiting embodiments, the method further includes determining an angle of the first joint based on the relative location of the first portion of the body with respect to the second portion of the body. In non-limiting embodiments, the at least two RF transponders of the first array are spaced apart by a distance equal to or less than $\lambda/4$, where $\lambda$ is a wavelength of the response signal for each of the at least two RF transponders of the first array. In non-limiting embodiments, each of the at least two RF transponders of the first array are arranged in-line with the first joint. In non-limiting embodiments, the at least two RF transponders of the second array are spaced apart by a distance equal to or less than $\lambda/4$, where $\lambda$ is a wavelength of the response signal for the at least two RF transponders of the second array, and wherein each of the at least two RF transponders of the second array are arranged in-line with the first joint.

According to another non-limiting embodiment, provided is a system for tracking a body, including: a plurality of arrays of radio frequency (RF) transponders arranged on a body, the plurality of arrays comprising a first array of RF transponders arranged on a first portion of the body and a second array of RF transponders arranged on a second portion of the body, the first portion of the body and the second portion of the body connecting at a first joint of the body; and at least one processor programmed and/or configured to: communicate, with an antenna, at least one activation signal to each RF transponder of the first array and the second array; receive, with the antenna, a plurality of response signals from the first array and the second array, the plurality of response signals comprising at least one response signal for each RF transponder of the first array and the second array; determine a difference in distances between the antenna and at least two RF transponders of the first array and a difference in distances between the antenna and at least two RF transponders of the second array based at least partially on at least a portion of the plurality of response signals; and determine a relative location of the first portion of the body and the second portion of the body based at least partially on the difference in distances between the antenna and the at least two RF transponders of the first array, a distance between the at least two RF transponders of the first array, the difference in distances between the antenna and the at least two RF transponders of the second array, and a distance between the at least two RF transponders of the second array.

In non-limiting embodiments, the at least one processor includes at least one first processor and at least one second processor, the system further including a reader device, the reader device including the at least one first processor and the antenna. In non-limiting embodiments, the difference in distances between the antenna and the at least two RF transponders of the first array is determined based on phases of response signals received from the at least two RF transponders of the first array. In non-limiting embodiments, the plurality of arrays of RF transponders further comprise a third array of RF transponders arranged on a third portion of the body and a fourth array of RF transponders arranged on a fourth portion of the body, wherein the third portion of the body and the fourth portion of the body connect at a second joint of the body.

In non-limiting embodiments, the system further includes a fabric material adapted to be worn on the body, wherein the plurality of arrays of RF transponders are integrated into the fabric material. In non-limiting embodiments, the antenna is arranged on the body. In non-limiting embodiments, the at least one processor is further programmed or configured to determine an angle of the first joint based on the relative location of the first portion of the body with respect to the second portion of the body. In non-limiting embodiments, the at least two RF transponders of the first array are spaced apart by a predefined distance and arranged in-line with the first joint, and wherein the at least two RF transponders of the second array are spaced apart by a predefined distance and arranged in-line with the first joint. In non-limiting embodiments, the at least two RF transponders of the first array are spaced apart by a distance equal to or less than $\lambda/4$, where $\lambda$ is a wavelength of the response signal for each of the at least two RF transponders of the first array, and wherein the at least two RF transponders of the second array are spaced apart by a distance equal to or less than $\lambda/4$, where $\lambda$ is a wavelength of the response signal for each of the at least two RF transponders of the second array.

According to another non-limiting embodiment, provided is a computer program product for tracking a body, wherein a plurality of arrays of radio frequency (RF) transponders are arranged on the body, the plurality of arrays comprising a first array of RF transponders arranged on a first portion of the body and a second array of RF transponders arranged on a second portion of the body, the first portion of the body and the second portion of the body connecting at a first joint of the body, the computer program product including at least one non-transitory computer-readable medium including program instructions that, when executed by at least one processor, cause the at least one processor to: communicate, with an antenna, at least one activation signal to each RF transponder of the first array and the second array; receive, with the antenna, a plurality of response signals from the first array and the second array, the plurality of response signals comprising at least one response signal for each RF transponder of the first array and the second array; determine a difference in distances between the antenna and at least two RF transponders of the first array and a difference in distances between the antenna and at least two RF transponders of the second array based at least partially on at least a portion of the plurality of response signals; and determine a relative location of the first portion of the body and the second portion of the body based at least partially on the difference in distances between the antenna and the at least two RF transponders of the first array, a distance between the at least two RF transponders of the first array, the difference in distances between the antenna and the at least two RF transponders of the second array, and a distance between the at least two RF transponders of the second array.

In non-limiting embodiments, the program instructions, when executed by the at least one processor, further cause the at least one processor to: determine an angle of the first joint based on the relative location of the first portion of the body with respect to the second portion of the body.

According to a further non-limiting embodiment, provided is a garment including: a first portion of material adapted to be worn on a first portion of a body, the first portion of material including a first array of radio frequency (RF) transponders arranged in-line with a first joint when the first portion of material is worn on the first portion of the body; and a second portion of material adapted to be worn on a second portion of the body, the second portion of material including a second array of RF transponders arranged in-line with the first joint when the first portion of material is worn on the first portion of the body, wherein the first portion of the body and the second portion of the body connect at the first joint.

In non-limiting embodiments, the first array of RF transponders includes at least two RF transponders integrated into the first portion of material. In non-limiting embodiments, the at least two RF transponders comprise conductive yarns. In non-limiting embodiments, the at least two RF transponders are spaced apart at a predefined distance. In non-limiting embodiments, the garment includes a shirt, wherein the first portion of material comprises a first portion of a first sleeve, wherein the second portion of material comprises a second portion of the first sleeve, and wherein the first joint comprises an elbow joint. In non-limiting embodiments, the garment includes a shirt, wherein the first portion of material comprises a first portion of a first sleeve of the shirt, wherein the second portion of material comprises a first portion of a torso section of the shirt, and wherein the first joint comprises a shoulder joint. In non-limiting embodiments, the garment includes pants and a shirt, wherein the first portion of material comprises a first portion of a torso section of the shirt, wherein the second portion of material comprises a first portion of the pants, and wherein the first joint comprises a hip or waist joint. In non-limiting embodiments, the garment includes pants, wherein the first portion of material comprises a first portion of a first pant leg, wherein the second portion of material comprises a second portion of the first pant leg, and wherein the first joint comprises a knee joint.

Other non-limiting embodiments or aspects will be set forth in the following numbered clauses:

Clause 1: A method for tracking a body comprising a plurality of arrays of radio frequency (RF) transponders arranged thereon, the plurality of arrays comprising a first array of RF transponders arranged on a first portion of the body and a second array of RF transponders arranged on a second portion of the body, the first portion of the body and the second portion of the body connecting at a first joint of the body, the method comprising: communicating, with an antenna of a reader device, at least one activation signal to each RF transponder of the first array and the second array; receiving, with the antenna, a plurality of response signals from the first array and the second array, the plurality of response signals comprising a response signal for each RF transponder of the first array and the second array; determining, with at least one processor, a difference in distances between the antenna and at least two RF transponders of the first array and a difference in distances between the antenna and at least two RF transponders of the second array based at least partially on at least a portion of the plurality of response signals; and determining, with at least one processor, a relative location of the first portion of the body and the second portion of the body based at least partially on the difference in distances between the antenna and the at least two RF transponders of the first array, a distance between the at least two RF transponders of the first array, the difference in distances between the antenna and the at least two RF transponders of the second array, and a distance between the at least two RF transponders of the second array.

Clause 2: The method of clause 1, wherein the difference in distances between the antenna and the at least two RF transponders of the first array and the at least two RF transponders of the second array are determined based on phases of the at least a portion of the plurality of response signals.

Clause 3: The method of clauses 1 or 2, wherein the plurality of arrays of RF transponders further comprise a third array of RF transponders arranged on a third portion of the body and a fourth array of RF transponders arranged on a fourth portion of the body, wherein the third portion of the body and the fourth portion of the body connect at a second joint of the body.

Clause 4: The method of any of clauses 1-3, wherein the plurality of arrays of RF transponders are integrated into a fabric material adapted to be worn on the body.

Clause 5: The method of any of clauses 1-4, wherein the reader device is arranged on the body and comprises the at least one processor.

Clause 6: The method of any of clauses 1-5, further comprising determining an angle of the first joint based on the relative location of the first portion of the body with respect to the second portion of the body.

Clause 7: The method of any of clauses 1-6, wherein the at least two RF transponders of the first array are spaced apart by a distance equal to or less than λ/4, where λ is a wavelength of the response signal for each of the at least two RF transponders of the first array.

Clause 8: The method of any of clauses 1-7, wherein each of the at least two RF transponders of the first array are arranged in-line with the first joint.

Clause 9: The method of any of clauses 1-8, wherein the at least two RF transponders of the second array are spaced apart by a distance equal to or less than λ/4, where λ is a wavelength of the response signal for the at least two RF transponders of the second array, and wherein each of the at least two RF transponders of the second array are arranged in-line with the first joint.

Clause 10: A system for tracking a body, comprising: a plurality of arrays of radio frequency (RF) transponders arranged on a body, the plurality of arrays comprising a first array of RF transponders arranged on a first portion of the body and a second array of RF transponders arranged on a second portion of the body, the first portion of the body and the second portion of the body connecting at a first joint of the body; at least one processor programmed and/or configured to: communicate, with an antenna, at least one activation signal to each RF transponder of the first array and the second array; receive, with the antenna, a plurality of response signals from the first array and the second array, the plurality of response signals comprising at least one response signal for each RF transponder of the first array and the second array; determine a difference in distances between the antenna and at least two RF transponders of the first array and a difference in distances between the antenna and at least two RF transponders of the second array based at least partially on at least a portion of the plurality of response signals; and determine a relative location of the first portion of the body and the second portion of the body based at least partially on the difference in distances between the antenna and the at least two RF transponders of the first array, a distance between the at least two RF transponders of the first array, the difference in distances between the antenna and the at least two RF transponders of the second array, and a distance between the at least two RF transponders of the second array.

Clause 11: The system of clause 10, wherein the at least one processor comprises at least one first processor and at least one second processor, the system further comprising a reader device, the reader device including the at least one first processor and the antenna.

Clause 12: The system of clauses 10 or 11, wherein the difference in distances between the antenna and the at least two RF transponders of the first array is determined based on phases of response signals received from the at least two RF transponders of the first array.

Clause 13: The system of any of clauses 10-12, wherein the plurality of arrays of RF transponders further comprise a third array of RF transponders arranged on a third portion of the body and a fourth array of RF transponders arranged on a fourth portion of the body, wherein the third portion of the body and the fourth portion of the body connect at a second joint of the body.

Clause 14: The system of any of clauses 10-13, further comprising a fabric material adapted to be worn on the body, wherein the plurality of arrays of RF transponders are integrated into the fabric material.

Clause 15: The system of any of clauses 10-14, wherein the antenna is arranged on the body.

Clause 16: The system of any of clauses 10-15, wherein the at least one processor is further programmed or configured to determine an angle of the first joint based on the relative location of the first portion of the body with respect to the second portion of the body.

Clause 17: The system of any of clauses 10-16, wherein the at least two RF transponders of the first array are spaced apart by a predefined distance and arranged in-line with the first joint, and wherein the at least two RF transponders of the second array are spaced apart by a predefined distance and arranged in-line with the first joint.

Clause 18: The system of any of clauses 10-17, wherein the at least two RF transponders of the first array are spaced apart by a distance equal to or less than $\lambda/4$, where $\lambda$ is a wavelength of the response signal for each of the at least two RF transponders of the first array, and wherein the at least two RF transponders of the second array are spaced apart by a distance equal to or less than $\lambda/4$, where $\lambda$ is a wavelength of the response signal for each of the at least two RF transponders of the second array.

Clause 19: A computer program product for tracking a body, wherein a plurality of arrays of radio frequency (RF) transponders are arranged on the body, the plurality of arrays comprising a first array of RF transponders arranged on a first portion of the body and a second array of RF transponders arranged on a second portion of the body, the first portion of the body and the second portion of the body connecting at a first joint of the body, the computer program product comprising at least one non-transitory computer-readable medium including program instructions that, when executed by at least one processor, cause the at least one processor to: communicate, with an antenna, at least one activation signal to each RF transponder of the first array and the second array; receive, with the antenna, a plurality of response signals from the first array and the second array, the plurality of response signals comprising at least one response signal for each RF transponder of the first array and the second array; determine a difference in distances between the antenna and at least two RF transponders of the first array and a difference in distances between the antenna and at least two RF transponders of the second array based at least partially on at least a portion of the plurality of response signals; and determine a relative location of the first portion of the body and the second portion of the body based at least partially on the difference in distances between the antenna and the at least two RF transponders of the first array, a distance between the at least two RF transponders of the first array, the difference in distances between the antenna and the at least two RF transponders of the second array, and a distance between the at least two RF transponders of the second array.

Clause 20: The computer program product of clause 19, wherein the program instructions, when executed by the at least one processor, further cause the at least one processor to: determine an angle of the first joint based on the relative location of the first portion of the body with respect to the second portion of the body.

Clause 21: A garment comprising: a first portion of material configured to be worn on a first portion of a body, the first portion of material comprising a first array of radio frequency (RF) transponders arranged in-line with a first joint when the first portion of material is worn on the first portion of the body; and a second portion of material configured to be worn on a second portion of the body, the second portion of material comprising a second array of RF transponders arranged in-line with the first joint when the first portion of material is worn on the first portion of the body, wherein the first portion of the body and the second portion of the body connect at the first joint.

Clause 22: The garment of clause 21, wherein the first array of RF transponders comprises at least two RF transponders integrated into the first portion of material.

Clause 23: The garment of clauses 21 or 22, wherein the at least two RF transponders comprise conductive yarns.

Clause 24: The garment of any of clauses 21-23, wherein the at least two RF transponders are spaced apart at a predefined distance.

Clause 25: The garment of any of clauses 21-24, wherein the garment comprises a shirt, wherein the first portion of material comprises a first portion of a first sleeve, wherein the second portion of material comprises a second portion of the first sleeve, and wherein the first joint comprises an elbow joint.

Clause 26: The garment of any of clauses 21-25, wherein the garment comprises a shirt, wherein the first portion of material comprises a first portion of a first sleeve of the shirt, wherein the second portion of material comprises a first portion of a torso section of the shirt, and wherein the first joint comprises a shoulder joint.

Clause 27: The garment of any of clauses 21-26, wherein the garment comprises pants and a shirt, wherein the first portion of material comprises a first portion of a torso section of the shirt, wherein the second portion of material comprises a first portion of the pants, and wherein the first joint comprises a hip or waist joint.

Clause 28: The garment of any of clauses 21-27, wherein the garment comprises pants, wherein the first portion of material comprises a first portion of a first pant leg, wherein the second portion of material comprises a second portion of the first pant leg, and wherein the first joint comprises a knee joint.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a," "an," and "the" include plural referents unless the context clearly dictates otherwise.

BRIEF DESCRIPTION OF THE DRAWINGS

Additional advantages and details are explained in greater detail below with reference to the exemplary embodiments that are illustrated in the accompanying schematic figures, in which:

FIGS. 2A-2E illustrate different arrangements of arrays of RF transponders on a body according to non-limiting embodiments;

FIG. 3A illustrates an arrangement for triangulating a single RF transponder with multiple antennas;

FIGS. 3B and 3C illustrate arrangements of arrays of RF transponders on a body according to non-limiting embodiments;

DESCRIPTION OF THE PREFERRED EMBODIMENTS

Figure 1:
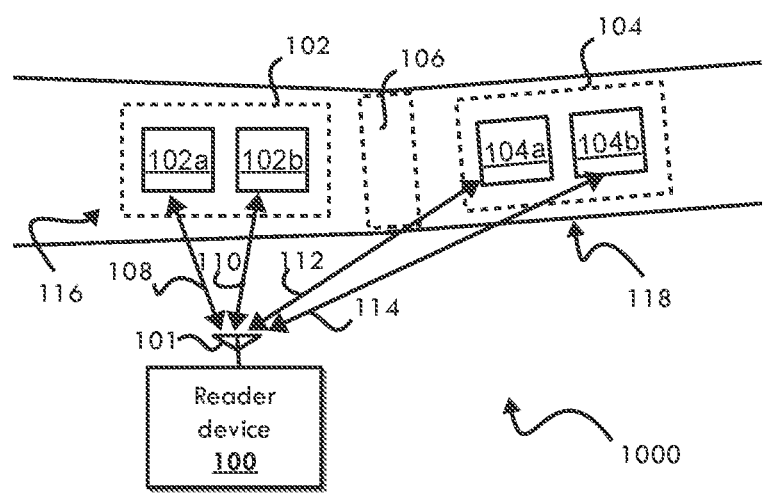
FIG. 1 is a schematic diagram of a system for tracking a body according to a non-limiting embodiment.

For purposes of the description hereinafter, the terms "end," "upper," "lower," "right," "left," "vertical," "horizontal," "top," "bottom," "lateral," "longitudinal," and derivatives thereof shall relate to the embodiments as they are oriented in the drawing figures. However, it is to be understood that the embodiments may assume various alternative variations and step sequences, except where expressly specified to the contrary. It is also to be understood that the specific devices and processes illustrated in the attached drawings, and described in the following specification, are simply exemplary embodiments or aspects of the invention. Hence, specific dimensions and other physical characteristics related to the embodiments or aspects disclosed herein are not to be considered as limiting.

As used herein, the terms "communication" and "communicate" may refer to the reception, receipt, transmission, transfer, provision, and/or the like, of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit processes information received from the first unit and communicates the processed information to the second unit.

FIG. 1 depicts a system 1000 for tracking a body according to a non-limiting embodiment. The system 1000 includes a reader device 100 and a plurality of passive radio frequency (RF) transponders 102a, 102b, 104a, 104b arranged on a body. The reader device 100 may include any device having an antenna 101 (or in communication with an antenna 101) and a processor and/or circuitry for activating and communicating with the plurality of passive RF transponders 102a, 102b, 104a, 104b. In non-limiting embodiments, the reader device 100 is a single-antenna handheld RFID-reader. In some non-limiting embodiments, the reader device 100 may also include a battery that can be periodically recharged. In some non-limiting embodiments, the reader device 100 may be a multi-purpose mobile device, such as a smartphone or portable computing device, configured with software and/or circuitry to transmit one or more activation signals, receive a plurality of response signals, and process the received signals. It will be appreciated that the reader device 100 may include any device capable of communicating with RF transponders 102a, 102b, 104a, 104b. Although the reader device 100 may include a plurality of antennas in some non-limiting embodiments, it will be appreciated that in such embodiments only one antenna needs to be used by the reader device 100 to communicate with the RF transponders 102a, 102b, 104a, 104b. The antenna 101 may be internal or external to the reader device 100.

In non-limiting embodiments, the RF transponders 102a, 102b, 104a, 104b are passive RFID tags that are incorporated into one or more materials adapted to be worn as one or more articles of clothing. In non-limiting embodiments, the RF transponders may be lightweight, machine-washable, battery-free, and ultra-high frequency (UHF) such that they can be incorporated into a wearable material without restricting a user's movement. For example, in non-limiting embodiments, each RF transponder 102a, 102b, 104a, 104b may include a limited amount of memory and therefore may contain a 96-bit or 128-bit serial number, rather than the 2 kilobytes of data that is sometimes included with RFID tags having Electronic Product Code (EPC) memory. In some non-limiting embodiments, the RF transponders may be constructed with conductive yarns woven directly into the material. It will be appreciated by those skilled in the art that any RF transponders may be used, with or without EPC memory, of different shapes, sizes, and manufacture.

With continued reference to FIG. 1, the RF transponders are arranged in a first array 102 of first RF transponders 102a, 102b and a second array 104 of second RF transponders 104a, 104b. The arrays 102, 104 of RF transponders may be arranged in various ways and in different geometries on portions of a body to be tracked. Each array 102, 104 may include two or more RF transponders spaced apart at a known distance. The distance (e.g., aperture) between each RF transponder may be predefined and known by the system (e.g., stored in memory and available to a processor of the reader device 100 or a separate processor). As an example, in some non-limiting embodiments, these values may be determined and recorded during manufacturing of a garment that includes a plurality of RF transponders arranged in a predefined manner. In other non-limiting embodiments, a user may configure parameters for the distances for each implementation. In non-limiting embodiments, each RF transponder 102a, 102b of the first array 102 may be arranged spaced apart at a distance of λ/4 or less, where λ is a wavelength of a response signal emitted by each of the RF transponders 102a, 102b. Likewise, each RF transponder 104a, 104b of the second array 104 may be arranged spaced apart at a distance of λ/4 or less, where λ is a wavelength of a response signal emitted by each of the RF transponders 104a, 104b. Such spacing facilitates the generation of valid and unique values of joint angle θ (e.g., with |cos θ|≤1).

Still referring to FIG. 1, the first array 102 is arranged on a first portion 116 of a body and the second array 104 is arranged on a second portion 118 of the body. In non-limiting embodiments, the first portion 116 of the body is connected to the second portion 118 of the body via a first joint 106. As an example, the first portion 116 of the body may be an upper arm, the second portion 118 of the body may be a forearm, and the first joint 106 may be an elbow joint. In other non-limiting embodiments, the first portion 116 may be a torso, the second portion 118 may be an upper arm, and the joint 106 may be a shoulder joint. In other non-limiting embodiments, the first portion 116 may be an upper leg (e.g., thigh), the second portion 118 may be a lower leg (e.g., calf), and the joint 106 may be a knee joint. It will be appreciated that one or more arrays of RF transponders may be arranged on any of two or more body parts connected by one or more joints. In non-limiting embodiments, the RF transponders 102a, 102b of the first array 102 are arranged substantially in-line with the joint 106, and the RF transponders 104a, 104b of the second array 104 are arranged substantially in-line with the joint 106. In this manner, a line connecting the centers of the RF transponders 102a, 102b of the first array 102 will intersect at the joint 106 with a line connecting the centers of the RF transponders 104a, 104b of the second array 104.

With continued reference to FIG. 1, in non-limiting embodiments the reader device 100 may be arranged on the body. For example, the reader device 100 may be in a user's pocket, attached to an article of clothing, or the like. In other non-limiting embodiments, the reader device 100 may be located off of the body (e.g., on a floor or supported by an object). The reader device 100, using an antenna 101, communicates one or more activation signals configured to activate the passive RF transponders 102a, 102b, 104a, 104b. The activation signal(s) energize each of the passive RF transponders which, in response to being energized, emit one or more response signals 108, 110, 112, 114. The one or more response signals 108, 110, 112, 114 are received by the antenna 101 of the reader device 100. Each of the RF transponders 102a, 102b, 104a, 104b are located at separate distances from the reader device 100. Each distance (e.g., an actual distance or a relative distance) may be determined by a processor of the reader device 100 or a separate processor based on an amount of time it takes for the response signals 108, 110, 112, 114 to be received by the reader device 100. As an example, the reader device 100 may determine a distance of each RF transponder 102a, 102b, 104a, 104b based on a phase of each of the response signals 108, 110, 112, 114. In non-limiting embodiments, the reader device 100 may support detecting the phase of the response signals 108, 110, 112, 114 with an accuracy of approximately 0.0015 radians, allowing for object location within millimeters. Various other arrangements are possible.

Still referring to FIG. 1, the reader device 100 may distinguish between response signals 108, 110, 112, 114, and therefore between RF transponders 102a, 102b, 104a, 104b, based on a modulation of each of the response signals 108, 110, 112, 114. For example, each RF transponder 102a, 102b, 104a, 104b may be configured to modulate the response signals (e.g., backscatter signals) using ON-OFF keying by changing an impedance of a respective antenna of the RF transponder. The reader device 100, in response to receiving the response signals 108, 110, 112, 114, may then demodulate each response signal to determine which response signal 108, 110, 112, 114 came from which RF transponder 102a, 102b, 104a, 104b based on a predefined modulation schema. It will be appreciated that various other methods may be used for uniquely identifying the response signals at the reader device 100. For example, in some non-limiting embodiments, a unique identifier corresponding to each RF transponder may be packaged in a respective response signal as a header or otherwise as part of the communicated data.

In non-limiting embodiments, the parameters defining the arrangement of RF transponders (e.g., transponder layout information), such as, but not limited to, a predefined spacing between RF transponders, a body part location of each array of RF transponders, expected modulation patterns, and/or the like, may be predefined and stored in memory that is accessible to the reader device 100 or a separate processor that processes the signals. For example, the transponder layout information may be stored in a network-accessible database such that the layout can be identified based on unique identifiers or modulations associated with the RF transponders. In some non-limiting embodiments, the transponder layout information may also be stored in EPC memory in one or each of the RF transponders. It will be appreciated that various other arrangements for storing transponder layout information may be used.

With continued reference to FIG. 1, based on the distances (e.g., actual distances or relative distances) of each of the response signals 108, 110, 112, 114 and a known distance between each of the RF transponders 102a, 102b of the first array 102 and a known distance between each of the RF transponders 104a, 104b in the second array 104, the reader device 100 or a separate processor determines a relative location of each array 102, 104. In this manner, based on the relative locations of each of the arrays 102, 104 (e.g., and therefore the relative locations of the corresponding body parts), a processor of the reader device 100 or a separate processor may be configured to determine an angle of the joint 106 based on an intersection of a first line extending from the RF transponders 102a, 102b in the first array 102 with a second line extending from the RF transponders 104a, 104b in the second array 104. In non-limiting embodiments in which multiple arrays of RF transponders are arranged on a body to track a plurality of joints, the body (e.g., skeleton) of a user may be tracked by determining the angles of each of the monitored joints. In such a manner, a user's movement, posture, and/or gestures may be monitored in real-time based on a real-time data stream and/or analyzed at a later time based on a received data stream and/or stored signal data.

Still referring to FIG. 1, based on the distances of multiple response signals 108, 110, 112, 114 received from the RF transponders 102a, 102b, 104a, 104b, the direction-of-arrival of the response signals may be determined. The direction-of-arrival is determined as the orientation of an array 102, 104 of RF transponders relative to the direction of the antenna 101 of the reader device 100. By using multiple RF transponders (e.g., at least two) in each array 102, 104, a single antenna may be used as opposed to existing methods that compute the direction-of-arrival of signals from a single RF transponder to multiple reader antennas arranged in different locations.

Referring now to FIGS. 2A-2E, various arrangements of arrays 202, 204 of RF transponders on a body are shown according to non-limiting embodiments. In the arrangement shown in FIG. 2A, movement of a shoulder joint is tracked by arranging a first array 202 on an upper arm and a second array 204 on a torso or chest. In the arrangement shown in FIG. 2B, movement of a knee joint is tracked by arranging a first array 202 on an upper leg (e.g., thigh) and a second array 204 on a lower leg (e.g., calf). In the arrangement shown in FIG. 2C, movement of an elbow joint is tracked by arranging a first array 202 on an upper arm (e.g., bicep) and a second array 204 on a lower arm (e.g., forearm). In the arrangement shown in FIG. 2D, movement of a waist joint is tracked by arranging a first array 202 on a torso and a second array 204 on a hip or waist. In the arrangement shown in FIG. 2E, movement of a hip joint is tracked by arranging a first array 202 on a torso and a second array 204 on an upper leg. It will be appreciated that the arrays 202, 204 of RF transponders may be arranged to track any joint on a body and that the examples shown in FIGS. 2A-2E are for illustration purposes only.

FIG. 3A illustrates an arrangement for locating a single RF transponder using multiple antennas according to known methods. By contrast, FIGS. 3B and 3C illustrate an arrangement of a system for tracking a body according to a non-limiting embodiment that overcomes the infrastructural requirements (e.g., multiple antennas) and improves the accuracy of determinations made using the arrangement shown in FIG. 3A. The system includes a single antenna 306 and arrays 302, 304 of RF transponders. As shown in FIG. 3B, the direction-of-arrival of signals received by a single antenna 306 from an array of RF transponders 302 is the orientation ($\theta_1$) of the array 302 relative to the direction of the antenna 306. As shown in FIG. 3C, in an example of tracking a user's leg, the orientation 61 of the user's thigh is measured relative to the antenna 306 using signals from the corresponding array 302 of transponders. This process is then repeated at the lower leg to obtain the orientation ($\theta_2$) of the other array 304 and the angle at the knee is then determined as $\theta_2-\theta_1$. With this arrangement, the precise location of the antenna 306 does not need to be known and therefore does not need to be determined or made static.

Figure 4A:
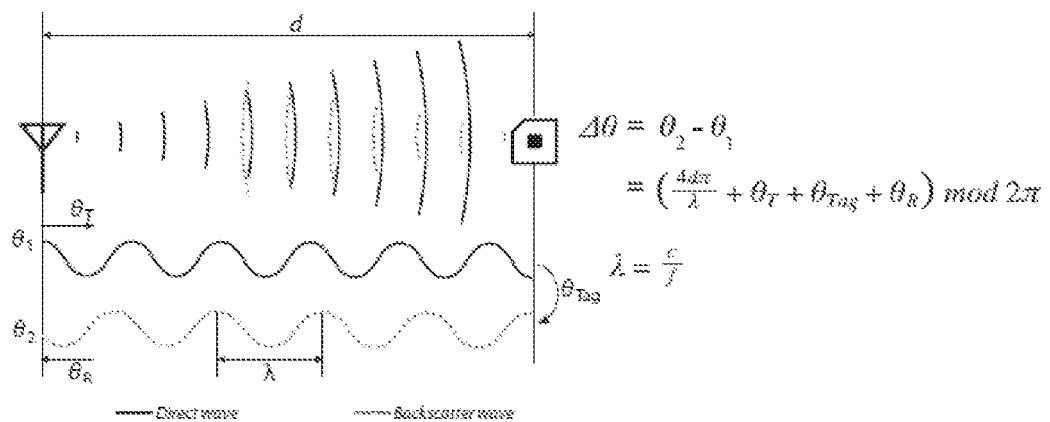
FIG. 4A illustrates RF transponder backscatter communication.
Figure 4B:
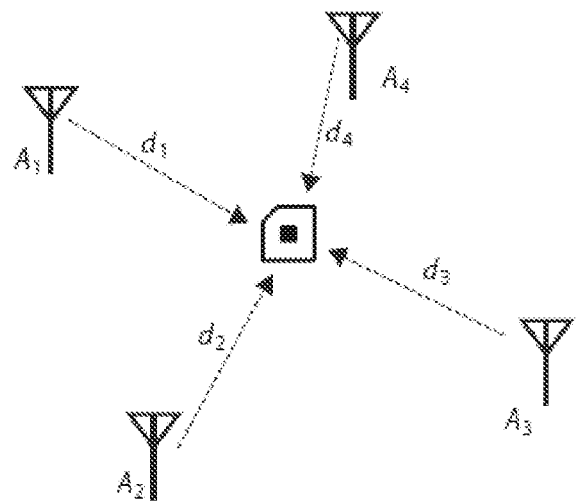
FIG. 4B illustrates an arrangement for triangulating a single RF transponder with multiple antennas.

Referring now to FIG. 4A, a backscatter communication process is shown according to known methods. As shown, passive RF transponders communicate with an antenna of a reader device by harvesting and reflecting (e.g., back-scattering) energy from the radio wave transmitted by the antenna. In the example shown in FIG. 4A, d is the distance between the antenna and the transponder, and the signal traverses a total distance of 2d back-and-forth in backscatter communication. FIG. 4B illustrates an arrangement of multiple antennas $A_1$-$A_4$ arranged at respective distances $d_1$-$d_4$ from a single RF transponder. In this arrangement according to known methods, the position of the antennas must be known and are fixed to triangulate the location of the RF transponder.

Figure 5:
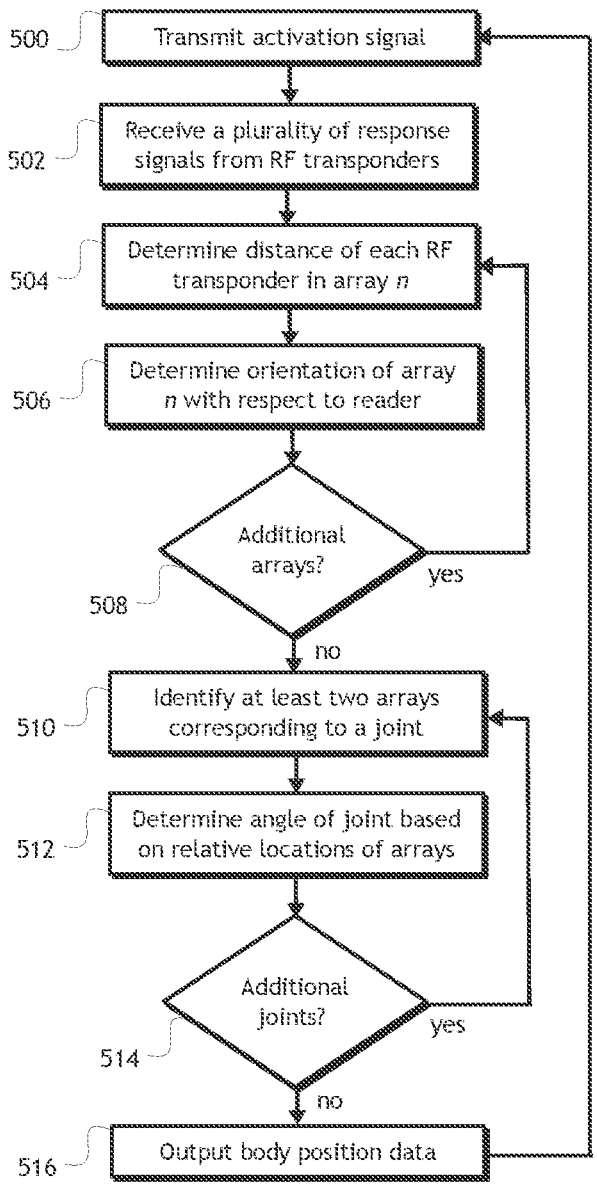
FIG. 5 is a flow diagram for a method of tracking a body according to a non-limiting embodiment.

Referring now to FIG. 5, a method for tracking a body is shown according to a non-limiting embodiment. It will be appreciated that the order of the steps shown in FIG. 5 is for illustration purposes only and that non-limiting embodiments may involve more steps, fewer steps, different steps, and/or a different order of steps. In non-limiting embodiments, the method may commence without needing to calibrate the system. The method starts at step 500 in which an activation signal is transmitted from an antenna of a reader device to a plurality of RF transponders arranged on a body. The activation signal may be communicated in a manner to energize a plurality of RF transponders within range of the antenna such that the transponders communicate a response signal in response to being energized. At step 502, the antenna receives at least one response signal from each of a plurality of transponders. In some examples, the plurality of transponders that respond may be less than the total number of RF transponders due to signal occlusion or other errors.

With continued reference to FIG. 5, once the reader device and antenna interrogate the plurality of RF transponders and receive response signals, at step 504 the distance between each RF transponder in a first array and the antenna is determined. This step may be performed after an interrogation, at regular intervals, or at any other times. Further, it will be appreciated that response signals from the RF transponders in multiple arrays may be processed before, after, at the same time, or at any other time relative to the signals from any other array. The distance may be determined from the time it takes a signal to be received. In this manner, the distance may be a relative distance of each RF transponder to the antenna that may be determined based on a difference in phase of the response signal. Small differences in distances among RF transponders in an array may be represented by a difference in phase. At step 506, an orientation of the array with respect to the antenna is determined based on the relative distances determined at step 504 and known distances between the RF transponders in the array.

Still referring to FIG. 5, at step 508, it is determined if there are additional arrays to process. It will be appreciated that other arrays may be processed in parallel or separately, and that the steps are shown as an example only. If there are additional arrays, the method proceeds back to step 504 and repeats steps 504 and 506 for a next array. Once all of the arrays are processed, the method proceeds to step 510 in which two arrays corresponding to a joint are identified. For example, a pair of arrays may include a first array arranged on a first body part and a second array arranged on a second body part, where the body parts are attached at a joint. At step 512, the relative locations of both arrays in a pair of corresponding arrays as determined at steps 504 and 506 are used to determine an angle of the joint connecting the body parts supporting those arrays.

At step 514 of FIG. 5, it is determined if there are additional joints to be analyzed. In examples where only a single joint is tracked, the method may proceed to step 516 to output the determined body position data (e.g., determined joint angles, body part orientations, etc.). The body position data may be outputted in any format such as, but not limited to, structured data, visual representations, and/or the like. The method may end at step 516 or loop back to step 500 to transmit another activation signal and measure the joint at a second interval. The steps may be looped for as many times as desired to track the movements of one or more joints and/or body parts over any period of time. If at step 514 there are additional joints to analyze, the method loops back to step 510 and repeats steps 510 and 512 to determine angles for as many joints in a body as desired. It will be appreciated that, in non-limiting embodiments, movement of a single joint, multiple body joints, or a full skeleton of a body may be tracked.

Figure 6:
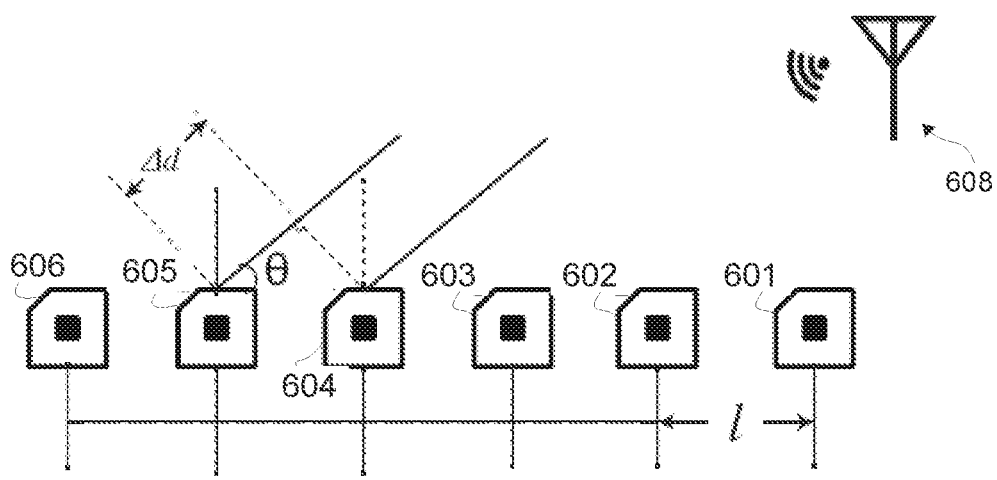
FIG. 6 is a schematic diagram of a system for tracking a body according to a non-limiting embodiment.

Referring now to FIG. 6, a linear array of RF transponders 601, 602, 603, 604, 605, 606 is shown according to a non-limiting embodiment. As shown, RF transponder 605 receives an incoming signal from an antenna 608 (of a reader device) at an angle θ. In the depicted example of FIG. 6, the distances (e.g., aperture I) between any two adjacent RF transponders are consistent across the linear array and are known and/or predefined. As an example, a processor of the reader device or a separate processor (not shown in FIG. 6) first determines the difference in time-of-arrival of the signals at transponder 604 and transponder 605, and then determines the difference in the distances those signals traversed, Δd. Based on Δd and I, the direction-of-arrival (θ) of the incoming signal from the antenna 608 to the uniform linear array can be determined based on the equation: Δd=I·cos θ (Eq. 1). The direction-of-arrival (θ) defines the orientation of the array of transponders in two-dimensional space. To determine Δd and therefore θ from phase rotations, the phase of the signals is measured at any two adjacent transponders (e.g., transponders 604, 605).

With continued reference to FIG. 6, although the value of Δd depends on the phase measurement of transponders 604, 605, the phase measurement may be affected by additional phase rotations that introduce error: $\theta_T$, $\theta_{T\ aд}$, and $\theta_R$, respectively, provided from the transmit chain of the reader device including the antenna 608, the receive chain of the transponder 605, and the receive chain of the reader device. To compute Δd accurately, these errors may be eliminated by relying on the relative phase between pairs of adjacent RF transponders. Because the difference in phase between any two RF transponders is used to determine distance, any phase offset from the reader device (e.g., $\theta_T$ and $\theta_R$) is automatically eliminated. Eliminating such errors may also be facilitated by utilizing RF transponders from the same manufacturer such that the quantity θт ад is also identical and cancels out, provided the RF transponders are oriented towards the same direction in space.

With continued reference to FIG. 6, the values $\theta_4$ and $\theta_5$ (not shown in FIG. 6) represent the raw phase observations of the backscatter radio signal from transponder 604 and transponder 605, respectively. With these values, the angle θ can be determined by:

$$\cos\theta = \frac{\Delta d}{l} = \frac{\lambda(\theta_5 - \theta_4)}{4\pi l}$$

(Eq. 2). This equation uses the value 4π as opposed to 2π because the radio signal travels twice the distance (i.e., to and from) in backscatter communication.

In addition to the RF phase rotation over the distance, the transmitter of the reader device, the transponder's reflection characteristics, and/or the receiver circuits of the reader device may also introduce additional phase rotation, denoted as $\theta_T$, $\theta_T$ ад and $\theta_R$, respectively. The reader device will therefore determine a phase difference (Δθ) of transmitted ($\theta_1$) and received signal ($\theta_2$), given by the equation: Δθ=$\theta_2$−$\theta_1$=(2d/λ*2π+$\theta_T$+θт ад +$\theta_R$) mod 2π; where λ=c/f such that λ is the wavelength of the radio signal at frequency f and c is the speed of light (Eq. 3). Various other factors may impact the phase rotations. For example, thermal noise from the reader device may introduce a mean measurement error of approximately 0.1 radians. The phase values measured at a given position may vary across different transponders (e.g., by a range of 0.30-5.84 radians) and orientations of transponders (e.g., by a range of 0 2π radians).

In non-limiting embodiments, a processor of the reader device or a separate processor may be configured to process signals that traverse multiple paths between the reader device and the RF transponders by reflecting off objects in the environment (e.g., walls, furniture, the user's body, and/or the like). These multiple signals may cause errors and prevent accurate tracking. To resolve such issues, the processor of the reader device or a separate processor utilizes a Multiple Signal Classification algorithm that is modified to apply to an array of passive RF transponders (e.g., as opposed to multiple reader antennas). The modified Multiple Signal Classification algorithm uses an Eigen sub-space decomposition approach to separate signal paths along different spatial angles. Mathematically, h=[$h_1$, . . . , $h_n$] represents the wireless channels from n RF transponders to the reader device, where each transponder is separated by a distance I. The absolute value square of these channels denotes received signal power from the RF transponders and the angle denotes the incoming signal phase. The normalized power, which is a probability metric, of the received signal P(α) along any arbitrary incident angle at the array α is represented as:

$$P(\alpha) = \frac{1}{|a(\alpha)E_N E_N^* a(\alpha)^*|},$$

where: $a(\alpha) = [e^{4\pi j r_i \cos(\alpha)/\lambda}]_{i=1,\ldots,N}$ where $r_i$ denotes the distance between the corresponding RF transponder to the center of the RF transponder array, $E_N$ is a matrix of the noise-Eigen vectors of hh*, and (·)* is the conjugate transpose operator (Eq. 4).

Signals traversing multiple paths may result in several possible angles that could represent the spatial orientation of the antenna of the reader device. This may be represented as a multiple local maxima of P(α), leading to ambiguity on the true orientation of the array of RF transponders with respect to the antenna. Multiple signal paths, like signals from "virtual sources," are mirror images of the reader device along various reflecting objects and/or surfaces. Many of these objects and/or surfaces are likely to be shared across adjacent body parts connected by a joint. Further, for each "virtual source" (e.g., reflecting surface), the angle-of-arrival $\theta_1$ and $\theta_2$ relative to two joints differs by the angle at the joint γ=$\theta_2$−$\theta_1$. Accordingly, for each "virtual source" (e.g., reflecting surface), there is two local maxima of P(α) across the two body parts that differ by γ. If all reflectors are quasi-static and shared across the two body-parts, P(α) of one body art would be a γ-rotated version of the other. Accordingly, the reader device or a separate processor may determine a value of γ by performing a cross-correlation of the two P(α) distributions to compute the relative shift. In some non-limiting examples, there may be smaller reflectors (e.g., small parts of the body) that may be a dominant influence on the signal for one body part having the first array, but not the other body part having the second array, leading to noise in the cross-correlation analysis. Accordingly, in non-limiting embodiments, the reader device or a separate processor may be configured to assign a sufficient number of dominant reflectors shared by adjacent body parts to provide high accuracy in joint angle-tracking.

Figure 7:
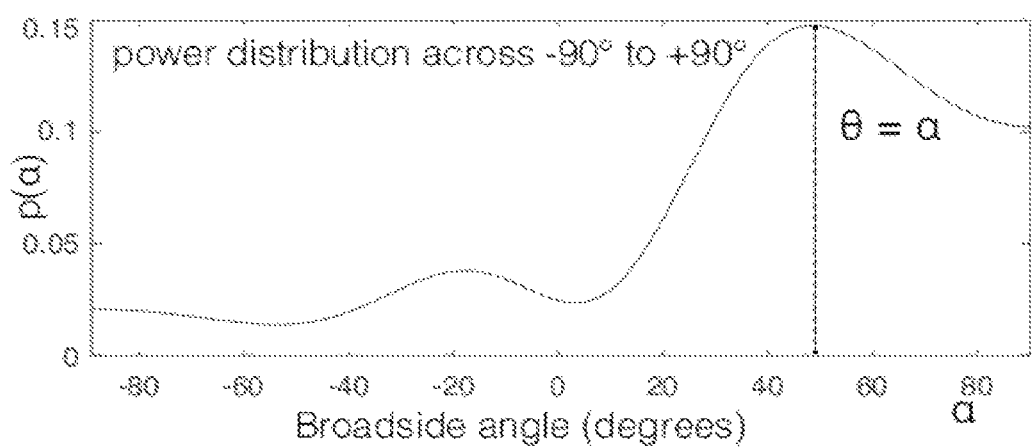
FIG. 7 is a chart showing an example of the relative power of a received signal along different angles-of-arrival α in system for tracking a body according to a non-limiting embodiment.

Referring now to FIG. 7, a chart is shown that illustrates an example of the relative power of the received signal along different angles-of-arrival α. The chart shows a distinctive peak at the angle (θ), which is the spatial angle-of-arrival of the signal from the reader device to the array of RF transponders. As shown, even in the presence of reflectors, the strongest peak of P(α) occurs typically at θ, with other paths producing smaller peaks.

Figure 8:
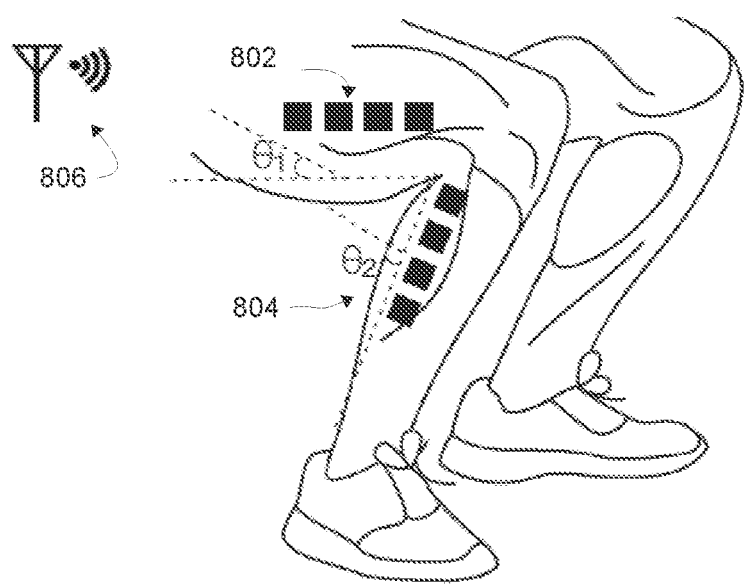
FIG. 8 illustrates an arrangement of arrays of RF transponders on a body according to a non-limiting embodiment.

Referring to FIG. 8, an example of an arrangement to track movement of a knee joint is shown according to a non-limiting embodiment. The reader device or a separate processor (not shown in FIG. 8) may be configured to process signals received by an antenna 806 that moves over time with the user. Using an arrangement of arrays 802, 804 of RF transponders on at least two parts of a user's body connected by a joint, the angle of such a joint is determined based on the relative orientation of the two adjacent parts of the user's body with respect to the antenna 806. As shown in FIG. 8, angle $\theta_1$ is formed from a first array 802 on an upper leg relative to the antenna 806 and angle $\theta_2$ is formed from a second array 804 on the lower leg relative to the antenna 806. In this example, the antenna 806 is arranged in the user's pocket or on the user's hip. The angle of the knee joint may therefore be determined based on the value of $\theta_2-\theta_1$. The accuracy of this determination may be affected by movement of the antenna 806 over the time period of collecting wireless channel measurements from the RF transponders of the arrays 802, 804. In non-limiting embodiments, a reader device is used that has a fast interrogation rate (e.g., 40 Hz or faster) to avoid error from normal human movement.

Figure 9:
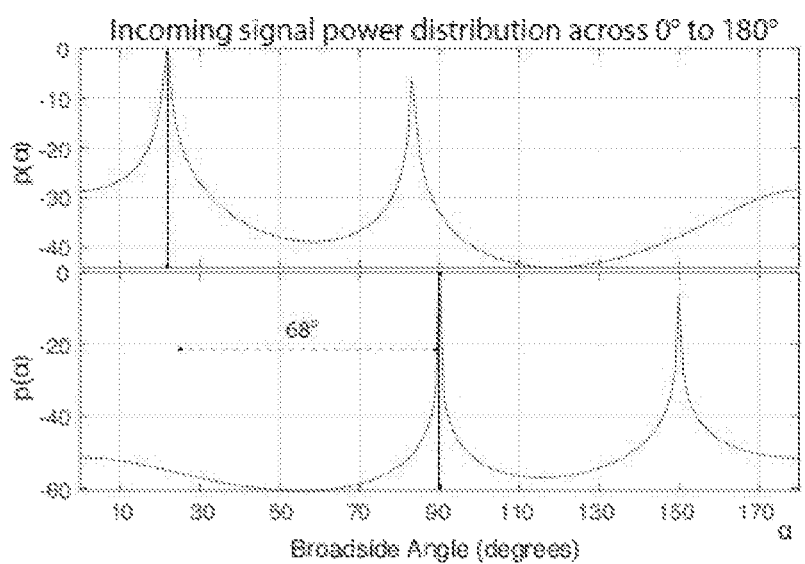
FIG. 9 is a chart showing examples of the relative power of a received signal along different angles-of-arrival α in system for tracking a body according to a non-limiting embodiment.

Referring now to FIG. 9, a chart is shown illustrating an example of the relative powers of the received signals along different angles-of-arrival α from the arrays 802, 804 shown in FIG. 8. The value of $\theta_2-\theta_1$ may be computed as the shift in Multiple Signal Classification spatial spectrum P(α) between the two arrays 802, 804.

In non-limiting examples, RF transponders may be chosen or designed based on how well the RF transponders interact with the human body and/or how minimally the phase of signals outputted by the RF transponders changes across different orientations. For example, RF transponders that perform consistently while both attached to a body and detached from a body may help reduce the amount of attenuation caused by the human body. Further, RF transponders may be chosen or designed based on radio sensitivity and/or directivity. RF transponders having a relatively weaker directivity may be desirable because a strong directivity may require the RF transponders to directly face the reader device. RF transponders may also be chosen or designed to be as small, thin, and flexible as possible, allowing for the RF transponders to be integrated into materials, such as garments, in a non-intrusive and non-restrictive manner. In non-limiting embodiments, the RF transponders may be Omni-ID IQ 150 RFID tags manufactured and sold by Omni-ID, Inc. It will be appreciated that various types of RF transponders may be used.

The reader device may be any suitable device having an antenna or in communication with antenna and configured to communicate one or more activation signals and receive a plurality of response signals. In non-limiting embodiments, the reader device may be an Impinj Speedway RFID reader equipped with a single Ettus VERT900 antenna, which provides a software interface for wireless channels. Although the Impinj Speedway RFID reader and other reader devices support multiple antennas, implementations of the system may involve disabling and/or not using all but one antenna. It will be appreciated that various types and implementations of reader devices may be used. To comply with regulations (e.g., FCC regulations in the United States), reader devices may be configured to "frequency hop" across 50 channels from 902 MHz to 928 MHz at an interval of approximately 0.2 seconds. Once the RF transponders are in an operational range of the reader device, the reader device may generate an observation data stream that contains all the low-level wireless channel data, including a Universally Unique Identifier (UUID), phase, signal strength, frequency, and/or the like.

In non-limiting embodiments, the reader device or a separate processor may track movement of a body in real-time. For example, the reader device or a separate processor may use a sliding window technique to extract quasi-simultaneous readings for different RF transponders from a data stream of received response signals. The reader device extracts the response signals of the same frequency from the data stream. The readings of each RF transponder occurs in a short time period (e.g., 0.1 seconds) such that, when the time period expires, the data is processed. Some of the RF transponders may not communicate back to the reader device due to potential body or object occlusion. However, in such instances, the set of incomplete data may still be processed even though accuracy errors may have been introduced during the collection process. For example, an angle of a joint may be inferred from two sequential readings of two adjacent arrays of RF transponders and the angle value may be inputted to a process or function that generates an estimate of the value based on a series of sequential measurements, such as but not limited to a Kalman filter. A sliding window process may generate numerous independent array readings (e.g., 30) per second. Depending on the processing power available, generating a spectrum profile for transponders in a single array may take approximately 0.015 seconds, allowing for real-time or near-real-time output. In non-limiting embodiments, predictions are performed based on each independent response signal from each transponder, thereby de-noising the results implicitly through transponder redundancy and transponder layout information.

In non-limiting embodiments, the system may be configured to track movement of a body and the angles of joints in three dimensions. Referring again to the example shown in FIG. 8, the angle of the knee joint is determined based on the difference $(\theta_2-\theta_1)$ of the angles between the arrays 802, 804 relative to the antenna 806. Using the one-dimensional arrays 802, 804 shown in FIG. 8 (e.g., four RF transponders arranged linearly), the value of $\theta_1$ is affected by movement of the antenna 806 in the same plane as the lower leg, even if the angle of the knee joint remains static. To address this potential source of error, non-limiting embodiments utilize two-dimensional arrays of RF transponders that include a rectangle of at least 2×2 transponders. For example, FIG. 2B illustrates an arrangement to track the knee joint using 4×2 arrays 202, 204 of RF transponders. Such a two-dimensional arrangement allows for decoupling the incoming direction-of-arrival of the reader device into azimuth and elevation angles.

Figure 10:
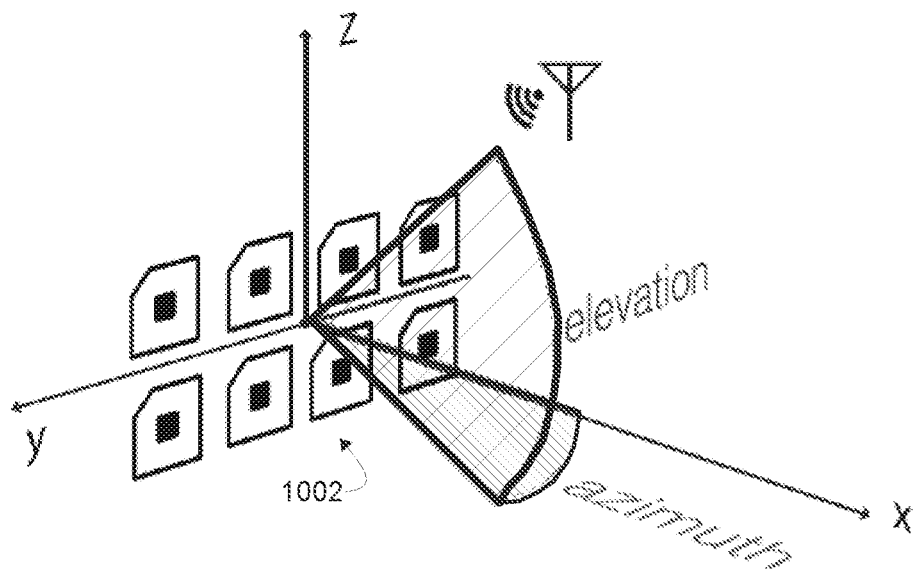
FIG. 10 illustrates a two-dimensional array of RF transponders according to a non-limiting embodiment.
Figure 11:
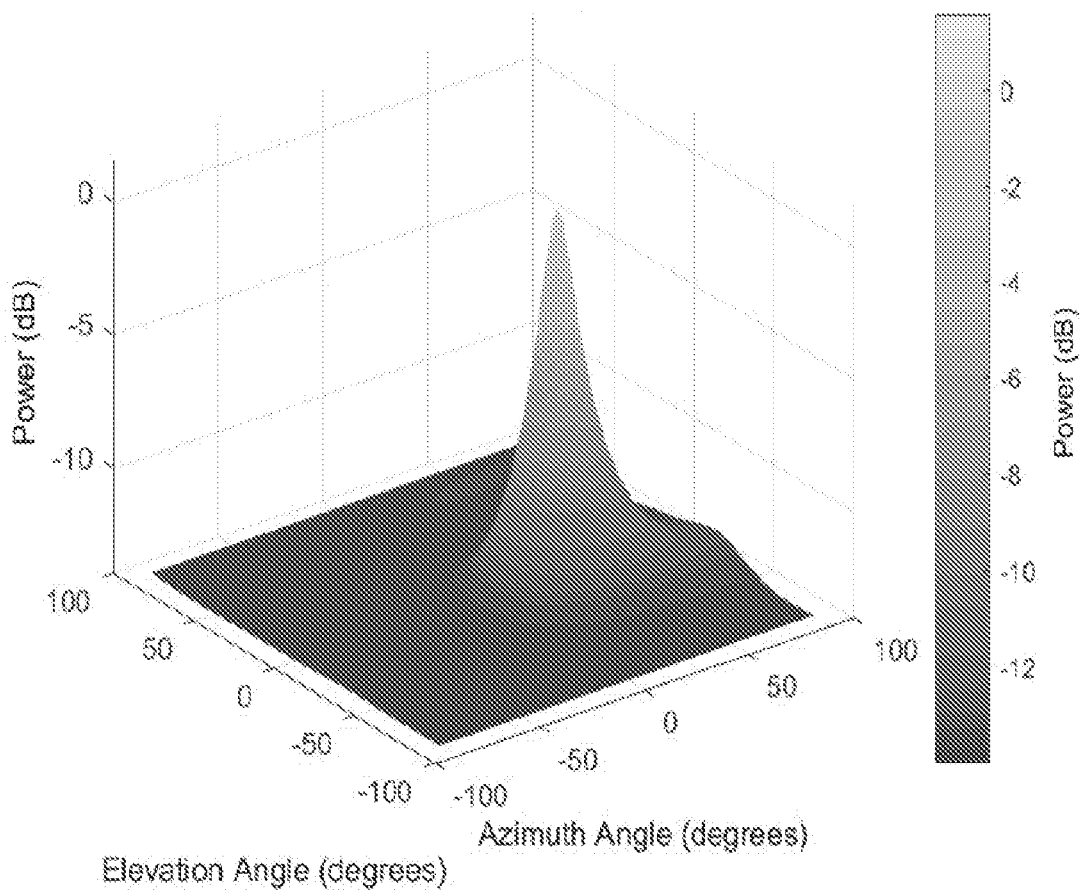
FIG. 11 is a graphical representation of the power of a received response signal along different azimuth and elevation angles according to a non-limiting embodiment.

Referring now to FIG. 10, an example of a two-dimensional array 1002 of RF transponders is shown according to a non-limiting embodiment. As shown, the long side of the array 1002 may be assigned to the y-axis and the short side of the array 1002 may be assigned to the z-axis. Thus, the direction of an incoming response signal can be represented using a combination of azimuth ($\phi_1$) and elevation ($\phi_2$). The azimuth value represents a polar angle in the x-y plane, with positive angles indicating counter-clockwise rotation of the origin point. The elevation value represents the angle above (positive angle) or below (negative angle) the x-y plane. The relative power of the received response signal along different angles-of-arrival is determined by the equation:

$$P(\alpha) = \frac{1}{|a(\phi,\psi)E_N E_N^* a(\phi,\psi)^*|},$$

where: $a(\phi,\psi) = [e^{4\pi j r_i \cos(\phi)\sin(\psi)/\lambda}]_{i=1,\ldots,N}$ where $r_i$ denotes the distance between the corresponding RF transponder to the center of the array of RF transponders (Eq. 5). FIG. 11 illustrates a three-dimensional graphical representation of the power of a received response signal along different azimuth and elevation angles.

Figure 12A:
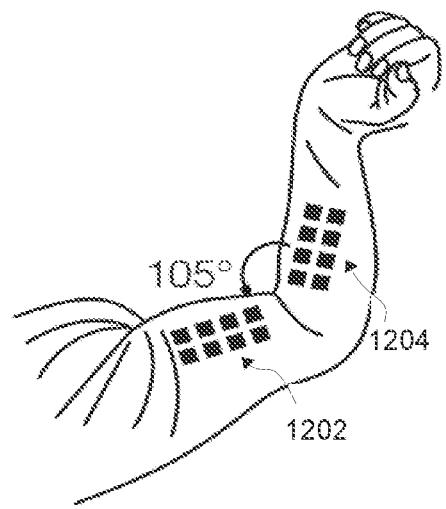
FIGS. 12A and 12B illustrate an arrangement of two arrays of RF transponders on an arm according to a non-limiting embodiment.
Figure 12B:
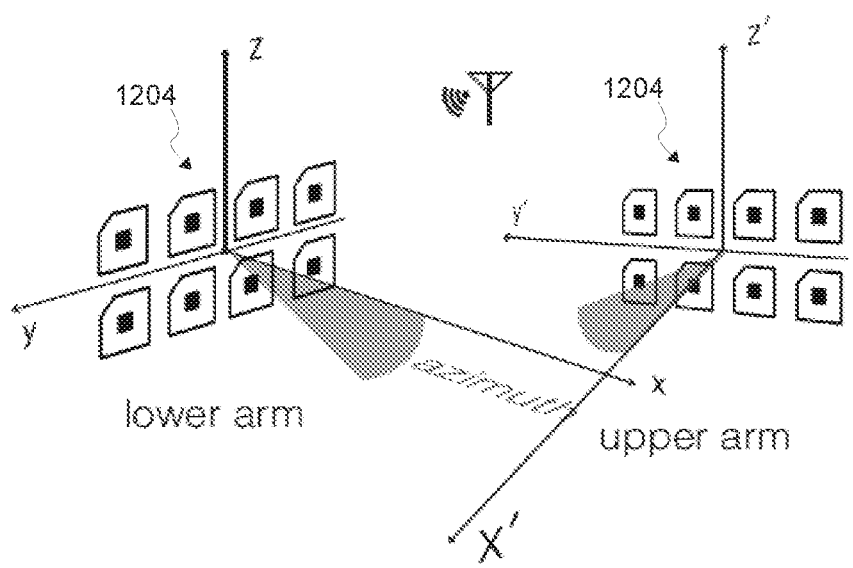

FIGS. 12A and 12B illustrate two views of an arrangement of a first array 1202 on an upper arm and a second array 1204 on a lower arm of a body according to a non-limiting embodiment. The upper arm and lower arm share the same z-axis. The azimuth and elevation angles of the two arrays 1202, 1204 may be determined by the equation provided herein (Eq. 5) for determining $P(\phi,\psi)$. Assuming $P(\phi,\psi)$ would be maximum at exactly $(\phi_1,\psi_1)$ and $(\phi_2,\psi_2)$ for the two arrays 1202, 1204, the elbow joint angle then can be determined by the value of $\phi_2-\phi_1$, the difference of two azimuth angles. Potential errors from multipath signals may be mitigated by determining the cross-correlation of $P(\phi,\psi)$ to find the difference in azimuth. Although FIGS. 12A and 12B show an arrangement for tracking movement of an elbow joint, it will be appreciated that such an arrangement may be applied to any joint including, but not limited to, knee joints, to track movement along one plane.

Non-limiting embodiments of the system for tracking a body described herein may also be arranged to track movement of joints that rotate along two degrees-of-freedom such as, but not limited to, a shoulder joint (e.g., a ball-and-socket joint). Since such joints do not rotate on any given plane, the relative angle between the two body parts that connect at such a joint cannot be represented in terms of a single angle in three-dimensional space. For example, for an arrangement in which a first array is on an upper arm and a second array is on a torso (e.g., as shown in FIG. 2A), two angles are used to represent the relative orientation of the upper arm and torso: (1) the relative azimuthal angle $\alpha$ along the plane of the torso; and (2) the polar angle $\beta$ that captures the elevation of the upper arm relative to the torso off-plane. These two angles are determined as the difference in azimuthal angles $\phi_2-\phi_1$ and polar angles $\psi_2-\psi_1$, respectively, of the two degrees of movement. For any rotations along one degree-of-freedom along the plane of the torso, this angle reduces to the difference in azimuthal angles $\phi_2-\phi_1$. Similarly, for rotations at a given relative azimuth, the upper arm would rotate on the plane perpendicular to the torso, while the torso remains static, such that $\psi_2-\psi_1$ would represent their relative angle out of the torso plane. Because these two rotations are independent, the rotations of the two-degree-of-freedom joint are represented by $\phi_2-\phi_1$ and $\psi_2-\psi_1$. These differences may be determined while accounting for multipath ambiguity by performing a cross-correlation of $P(\phi,\psi)$ per array, both along azimuth and polar axes, and then determining the difference across arrays.

The angle differences $\phi_2-\phi_1$ and $\psi_2-\psi_1$ are defined in a coordinate system relative to the direction of the antenna of the reader device. Re-orienting this coordinate system to an accurate three-dimensional coordinate system may be based on knowledge of the location of the antenna of the reader device. In non-limiting embodiments, the processor of the reader device or a separate processor is configured to determine the location of the antenna of the reader device via triangulation using multiple RF transponders arranged on the body at known relative locations. For example, the location of the antenna may be determined as an optimization problem solved by using a stochastic gradient descent algorithm with multiple randomly chosen initial estimates of the location of the antenna. Once the location of the antenna is known, the coordinates $(\phi,\psi)$ are translated to the coordinate system of the body. For example, a processor of the reader device or a separate processor may determine the coordinate transform of the family of $(\phi,\psi)$ coordinates in $P(\phi,\psi)$ to account for multipath ambiguity. The processor may then determine the relative angle differences as described herein.

Figure 13:
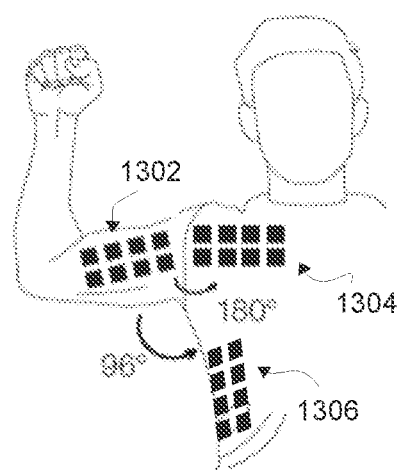
FIG. 13 illustrates an arrangement of three arrays of RF transponders on a body according to a non-limiting embodiment.

Referring now to FIG. 13, an arrangement including an additional array 1306 of RF transponders is shown according to a non-limiting embodiment. The additional array 1306 may be arranged on a body part such that the body part supports two separate arrays 1304, 1306 and connects, via a joint, to a body part that supports at least one array 1302. The additional array 1306 may be arranged orthogonal to the existing array 1304 on the body part. For example, the additional array 1306 may be arranged along the side of the torso orthogonal to array 1304 to track the shoulder joint. This additional array 1306 provides a secondary source of data, where the roles of azimuthal and polar angles are inverted, which can be used to resolve ambiguities in the primary data received and processed. While body frame tracking angles off-plane may have an ambiguity of ±90°, this ambiguity may be resolved by use of the additional array 1306. It will be appreciated that the additional array 1306 may be placed on any body part and at other known respective angles to the array 1304. In this manner, the processor of the reader device or a separate processor is able to distinguish, with the polar angle, between off-plane angles that are "upwards" and angles that are "downwards" due to the symmetry for an array in such a scenario along a given plane.

In non-limiting embodiments, the reader device or a separate processor may be configured to track movement of joints along three-degrees-of-freedom such as, but not limited to, a wrist joint or ankle joint. For example, additional arrays of RF transponders may be arranged along three mutually orthogonal axes at the joint to track such joints.

In non-limiting embodiments in which the arrays of RF transponders are integrated into a material adapted to be worn on a body, such as a garment, errors may be introduced from the flexibility of the material. Accordingly, in non-limiting embodiments, the processor of the reader device or a separate processor may be configured to account for material flexibility that could affect the geometry of the arrays of RF transponders. While the plurality of RF transponders in each array is ideally flat on a rigid surface, flexibility of the material results in uneven transponders in an array which may affect both the relative distance and orientation of the transponders. In non-limiting embodiments, a processor of the reader device or a separate processor may be programmed to execute a modified algorithm to account for such errors. The modified algorithm may be based on a number of properties of the material. For example, the expected change in distance between any two RF transponders for most fabric materials may be limited to a few centimeters. As a result, transponders are on average expected to move closer to each other, rather than farther away, because a folding of the material is more common than a stretching of the material during wear. The folds generated in a material are likely to remain even as the user moves their joints. Further, the relative ordering of RF transponders, which may be separated by several centimeters, is unlikely to change due to the flexibility of the material.

In non-limiting embodiments, to account for material flexibility, a Multiple Signal Classification algorithm may be modified to be based on the expected scaling factor μ in relative distances between RF transponders in an array. Such a modified algorithm measures a predetermined expected scaling factor of the distance between pairs of RF transponders, taking into account the flexibility of the material. These standard deviations may be experimentally derived for a material and programmed into the RF transponders (e.g., at the time of manufacture or otherwise) such that the transponders can provide this information to the reader device when interrogated. As described herein, it will be appreciated that such transponder layout information may be stored anywhere and obtained by the processor of the reader device or a separate processor. To illustrate the mathematical generalization for arrangements using a two-dimensional array of transponders, $P(\alpha)$ can be determined with the following equation:

$$P(\alpha) = \frac{1}{|a(\alpha) E_N E_N^* a(\alpha)^*|},$$

where: $a(\alpha) = [e^{4\pi j r_i \mu \cos(\alpha)/\lambda}]_{i=1,\ldots,N}$ where $r_i$ denotes the distance between the corresponding tag to the center of the RF transponder array, $E_N$ is a matrix of the noise-Eigen vectors of hh*, and (·)* is the conjugate transpose operator (Eq. 6).

The modified algorithm to account for a flexibility of the material estimates the orientation of the array of RF transponders by taking into account an average-case estimate of the separation between individual RF transponders. However, in practice, the shift between RF transponders may vary about the mean, thereby introducing errors to the estimate of orientation. Given that flexibility of the material is likely to introduce similar quantum-of-error in the orientation of the two parts, these errors may be at least partially cancelled out. Flexing of the material may cause the orientation of individual RF transponders to change, leading to changes in the phase values for the received response signals. In many examples, the orientation of an RF transponder may change by less than 10°, which results in a tolerable phase observation noise. Moreover, the modified Multiple Signal Classification algorithm relies on the phase differences of multiple pairs of RF transponders, which further removes noise from the measurements.

Figure 14:
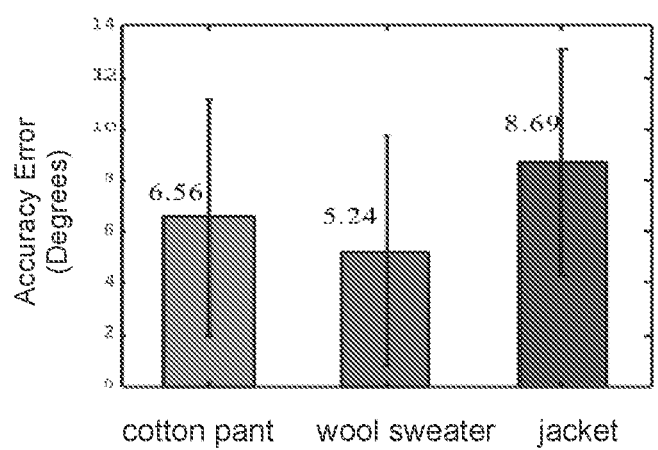
FIG. 14 is a chart of test results of different materials according to non-limiting embodiments.

In non-limiting embodiments, the type of material used may be chosen based on considerations of material flexibility. The quantum-of-error due to flexibility depends at least partially on the nature of material used. FIG. 14 shows test results for three different types of material in which the value of μ was computed. Testing was performed on the following materials and garments: (1) cotton pants; (2) a wool sweater; and (3) a polyester jacket, each having different material flexibilities. The tests were performed with the material placed on the ground with an intentional fold, and data was collected five times. FIG. 14 illustrates the mean and standard deviation of the error in the angle of a one-degree-of-freedom joint using RF transponders mounted on each of the three different types of material. A mean error of 6.6°, 5.2° and 8.7° was determined for cotton pants, a wool sweater, and a polyester jacket, respectively.

In non-limiting embodiments, the system and method for tracking a body may be used in various different contexts and scenarios. For example, by wearing a garment including an arrangement of arrays of RF transponders and a portable reader device, the health of patients may be tracked without wearing heavy or otherwise unwieldy equipment. This may include a patient's posture during different activities (e.g., walking, running, sitting, climbing, laying, driving, lifting, etc.). Further, in some non-limiting embodiments physiological conditions may be detected, such as tremors, areas of pain, biological reactions, and/or the like. In some non-limiting embodiments, the health and safety of employees or other workers may be monitored by the workers wearing garments including an arrangement of RF transponders such that movements and actions that result in workplace injuries can be monitored and discouraged. For example, it may be desirable to monitor the movement of a worker that lifts heavy objects or engages in other physical activities that could result in injury without using a proper lifting or posture technique. A user's movements may also be tracked for fitness tracking applications, such as to measure a number of steps, a gait, step lengths, a posture, and/or the like. Non-limiting embodiments may also be used to capture a user's motions for playing games (e.g., a motion-based game, a virtual reality or augmented reality game, and/or the like) or for animation and/or film making (e.g., capturing a user's motion for rendering animations, for three-dimensional films, and/or the like). Non-limiting embodiments may also be used for sports training. For example, an athlete's posture, movement, and technique for tennis, golf, baseball, and/or other like sports may be analyzed while wearing non-invasive and non-intrusive cloths incorporating arrays of RF transponders.

In non-limiting embodiments, the size of the array and the distance between each transponder in the array may be varied to improve the accuracy of the determinations. Increasing the number of transponders in each array and the distance between each transponder likewise improves the accuracy of the determinations. Different configurations of transponders were testing according to the following parameters:

| tag array dimension | aperture (cm) | tag array size (cm$^2$) |
|---|---|---|
| 2 × 3 | 5 | 7.5 × 12.5 |
| 2 × 4 | 5, 4 | 7.5 × 17.5, 6.5 × 14.5 |
| 2 × 5 | 4 | 6.5 × 18.5 |
| 3 × 3 | 5, 4, 3 | 12.5 × 12.5, 10.5 × 10.5, 8.5 × 8.5 |
| 4 × 4 | 5, 4, 3 | 17.5 × 17.5, 14.5 × 14.5, 11.5 × 11.5 |
| 5 × 5 | 5, 4, 3 | 22.5 × 22.5, 18.5 × 18.5, 14.5 × 14.5 |

Figure 15:
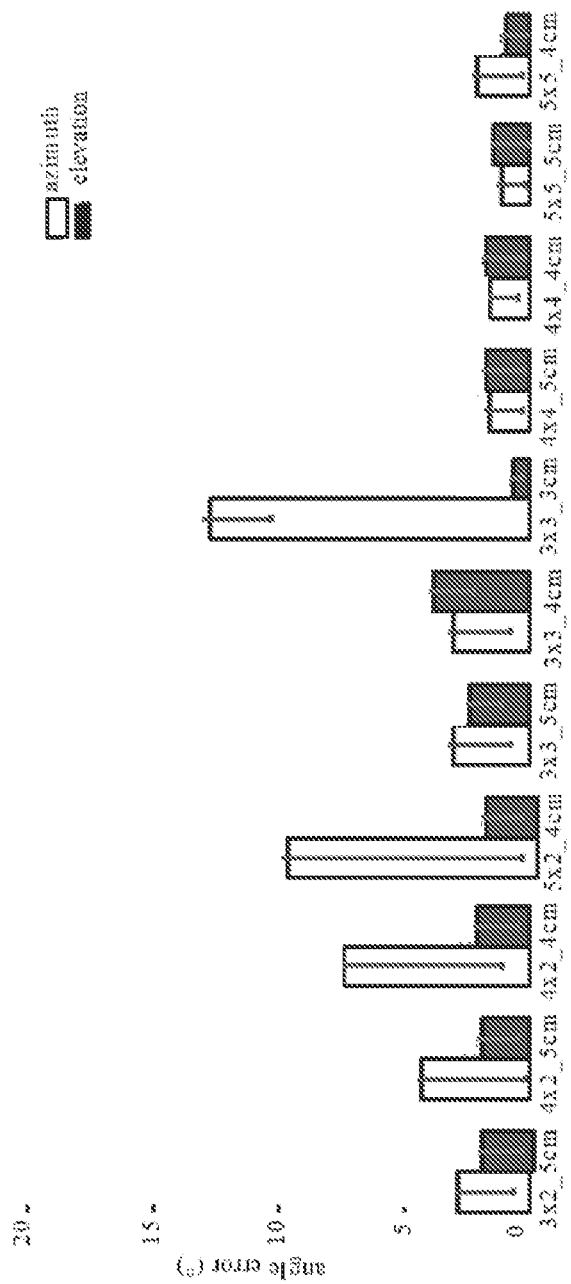
FIG. 15 is a chart of test results of different arrangements of RF transponders according to non-limiting embodiments.

Tests in each of these configurations were performed with Alien Square ALN-9629 RFID tags mounted on a rigid wooden platform. The reader device was placed on a floor and the tag array was arranged 1 meter away from the antenna, facing the same direction and standing on the floor. Tests were executed on six different angles relative to the antenna: 30°, 60°, 90°, 120°, 150°, and 180°. For each position, the test collected data for 30 seconds with three repetitions. Different array configurations with an aperture of 3-5 cm and a size of 6-25 transponders were then tested. FIG. 15 illustrates a chart of test results showing the error of both azimuth and elevation measurements by degree. As shown, the lowest error measured results from an arrangement of 5×5 transponders spaced 5 cm apart.

Experiments were performed on three joints in an arrangement of a non-limiting embodiment for testing. The three joints tested include the right elbow (e.g., one-degree-of-freedom in upper body), left knee (e.g., one-degree-of-freedom in lower body), and left shoulder (e.g., two-degrees-of-freedom in upper body). The angular error of relative location determinations of the body parts corresponding to each joint were evaluated in a laboratory environment using a motion capture system. The tests were performed using Omni-ID IQ150 RF transponders, manufactured by Omni-ID, Inc., and a RFMAX S9028 antenna arranged on the ground to allow for the subject wearing the RF transponders to move around naturally within 0.5 meters from the antenna. To obtain ground-truth joint angles during motion, an eight-camera Optitrack system was set-up inside the laboratory space. The eight motion capture cameras were deployed on the ceiling and multiple reflector markers were affixed to different body parts. The arrangement was calibrated such that the Optitrack system could track the markers with sub-millimeter accuracy.

To test a knee joint, two rectangular arrays of RF transponders (4×2 transponders) were affixed to the front side of a subject left pant leg. A first array was affixed to the lower leg and a second array affixed to the upper leg. The subject marked time and walked around the antenna in a normal walking pose. For each context (marked time and walking around the antenna), data was collected for 60 seconds. The subject stood still at the beginning and the ending of this time period for ground truth calibration purpose. To retrieve the ground truth, six reflectors were placed on the left side of the left legs. Two imaginary lines (the top three and lower three reflectors, respectively) were determined using the motion capture data, and then the angle between these two lines was computer. Because the angle measured from the side (e.g., motion capture) is not identical to that from the front (e.g., as in non-limiting embodiments of the system described herein), the angle was measured different at the beginning (e.g., when the subject was still) to compute the constant offset. The offset in the subject tested was 22°. Based on absolute timestamps, the motion capture data was then aligned with the predictions generated by the system arrangement.

Figure 16A:
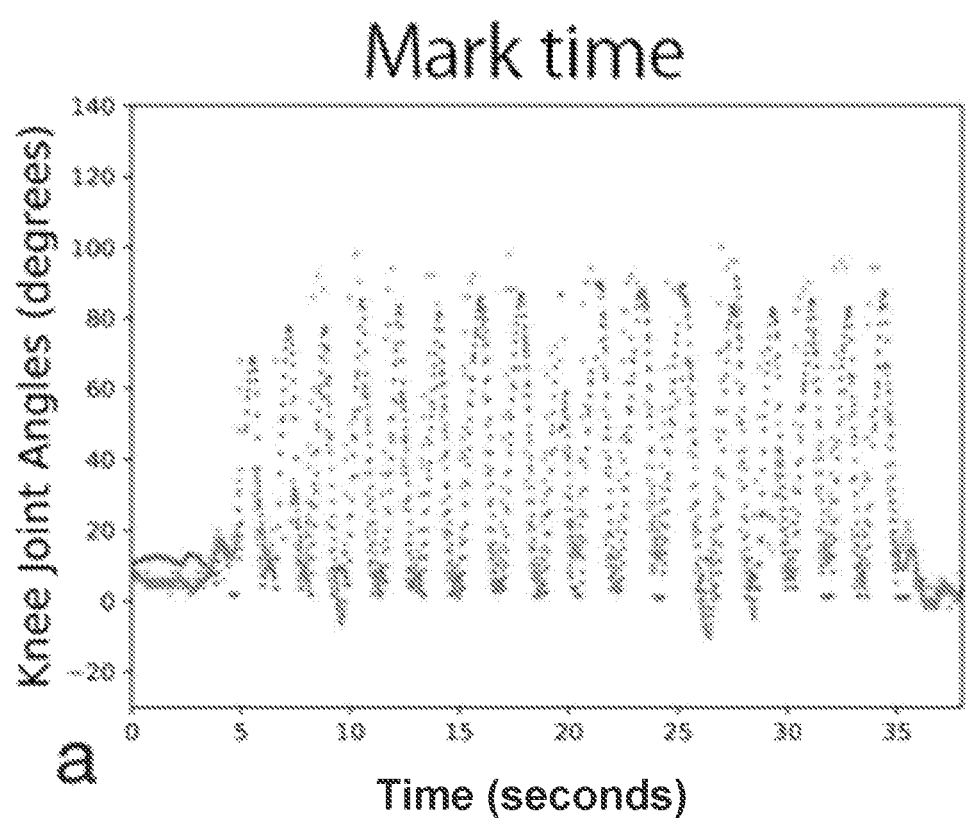
FIGS. 16A-D are charts showing test results for knee joint experiments according to non-limiting embodiments.
Figure 16B:
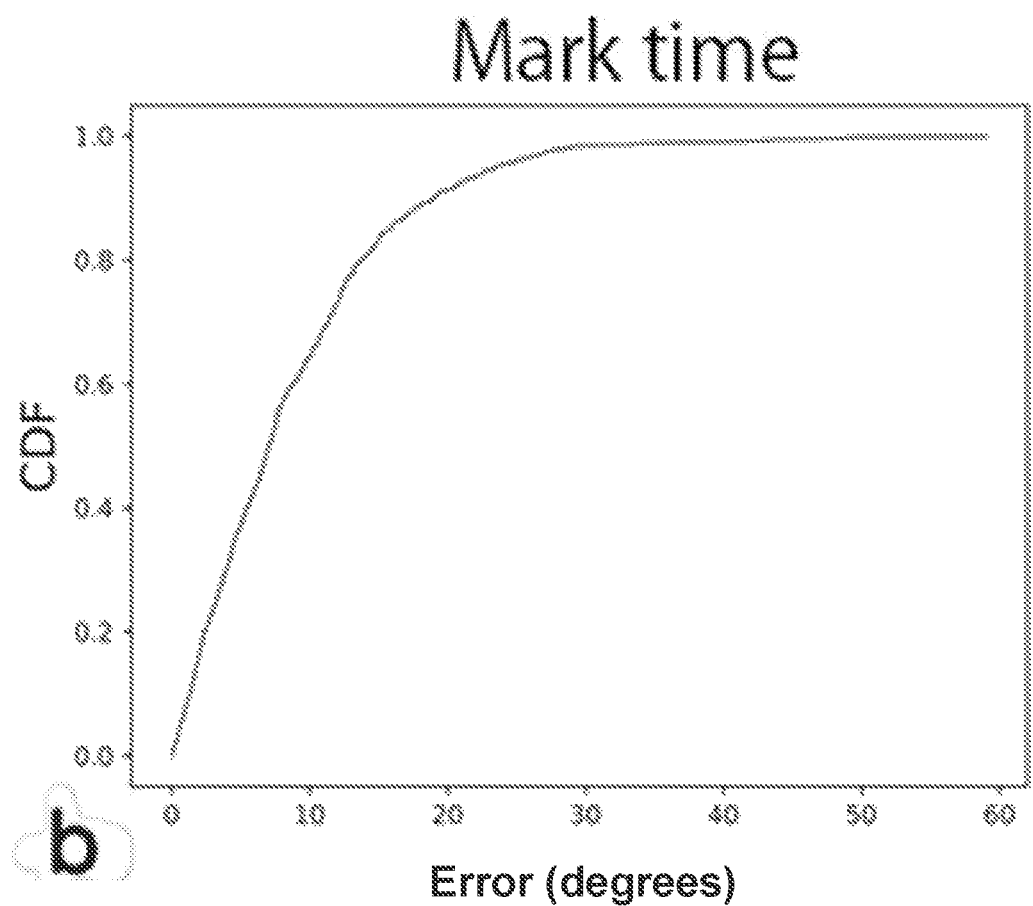
Figure 16C:
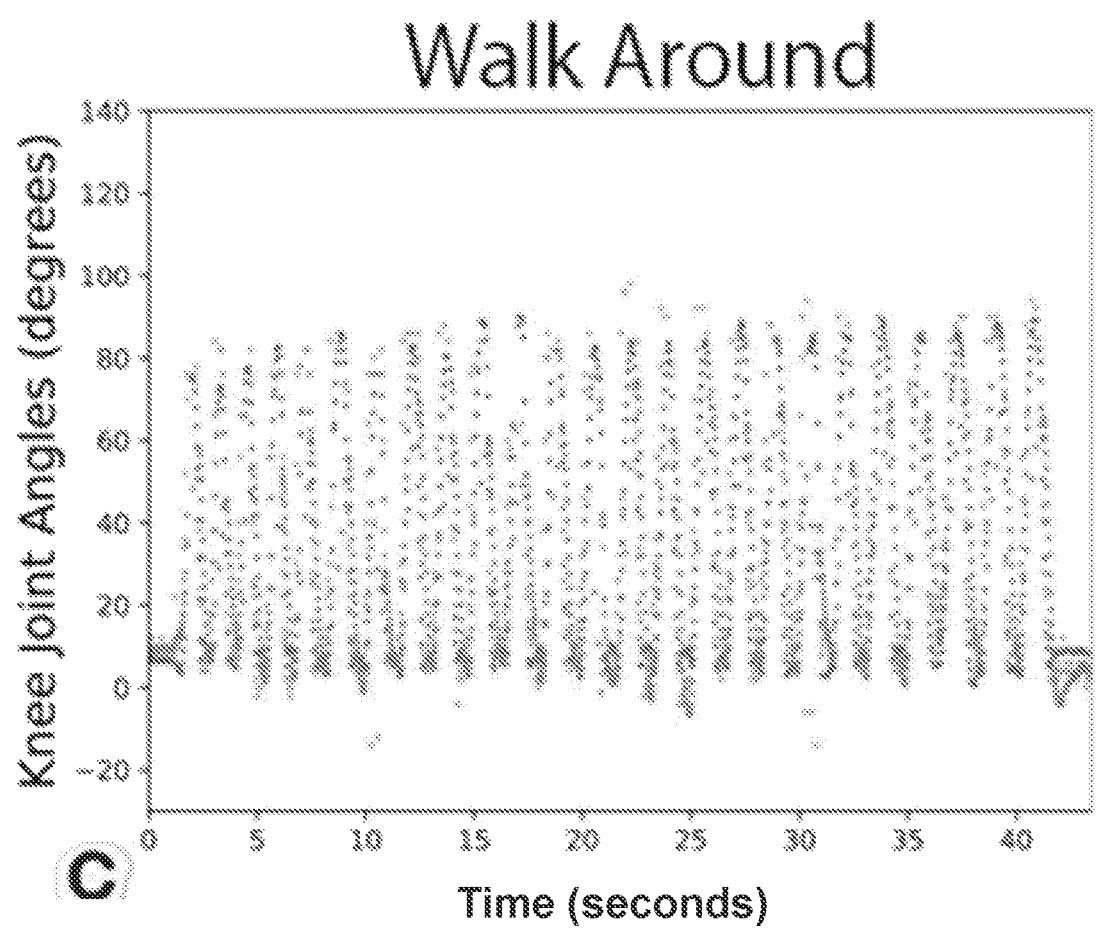
Figure 16D:
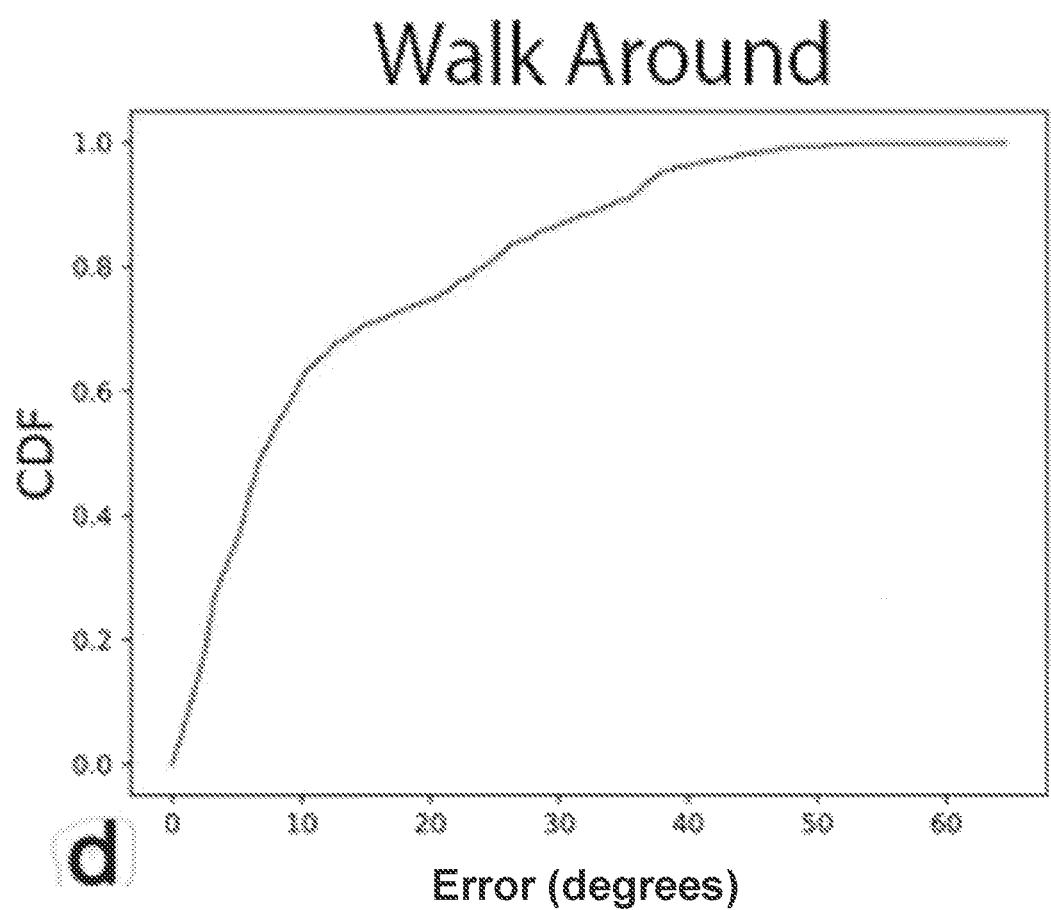

FIGS. 16A-D illustrate charts plotting evaluation results for the knee joint experiments. FIGS. 16A and 16B show results for the marked time context, in which the subject lifted his leg 17 times (counting the peaks in FIG. 16A) during a 30 second period. The system captured 1105 independent transponder array readings. The refresh rate was 36.8 Hz. A standard Kalman filter was also implemented to smooth the system's predictions. FIG. 16B illustrates the angular error distribution after applying the Kalman filter in a CDF chart (average error=8.89°, standard deviation=) 7.73°. FIGS. 16C and 16D illustrate results for the walking around context, in which the subject lifted his leg 25 times in 40 seconds (FIG. 16C). The system captured 1585 independent transponder array readings. The refresh rate was 39.6 Hz. FIG. 16D illustrates the corresponding angular error distribution after applying a Kalman filter in a CDF chart (average error=12.50°, standard deviation=12.52°).

Based on the experiments, it was determined that non-limiting embodiments of the system and method accurately track the angle of the knee joint akin to a baseline with high responsiveness, refresh rate, and accuracy. When users walk around the antenna, the system still functions correctly, although the error increases by 4°. It was observed that, as the user walks around, the reader antenna inevitably moves over time on his or her body.

To test an elbow joint, two rectangular arrays of RF transponders (4×2 transponders) were affixed to the bottom of the sleeve of a cotton sweater in-line with the elbow joint. One array was arranged on the lower arm of the sweater and the other array on the upper arm of the sweater. The subject was instructed to move the elbow joint as well as the shoulder to test diverse relative positions from the antenna to the arrays. A long one-shot data collection was then performed for 3 minutes and the subject was instructed to change the movement pace intentionally during the evaluation. To retrieve the ground truth, six reflectors were placed on the top of the sleeve of a cotton sweater. The systematic offset in the elbow testing example subject was 0°.

Figure 17A:
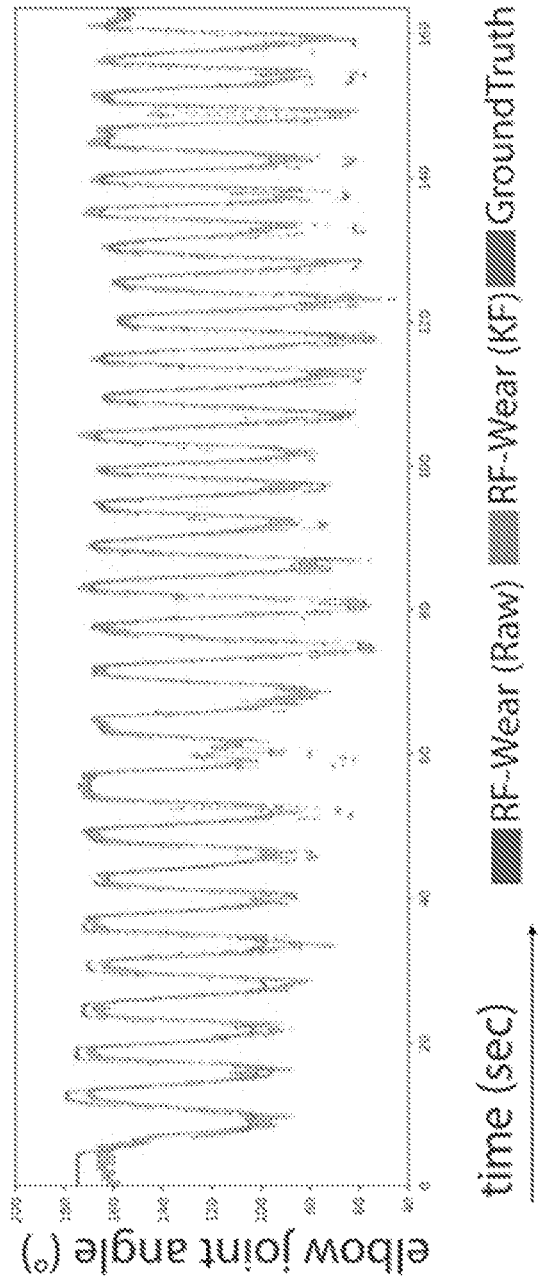
FIGS. 17A-B are charts showing test results for elbow joint experiments according to non-limiting embodiments.
Figure 17B:
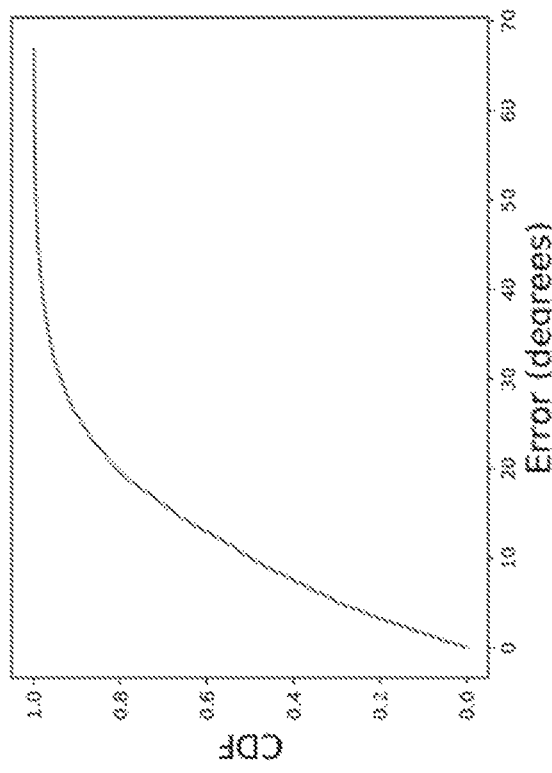
Figures 17A, 17B:
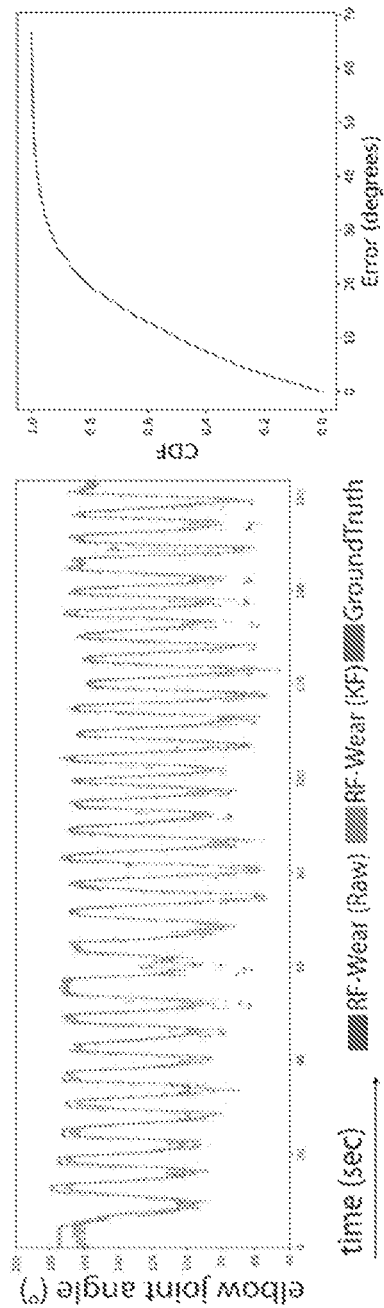

FIGS. 17A and 17B illustrate charts plotting evaluation results for the elbow experiments. During the test, and as shown in FIG. 17A, the subject repeated the elbow gestures for 27 times in 155 seconds. Both the raw predictions and the Kalman filter predictions were well aligned with the ground truth measurements from the motion capture system. FIG. 17B illustrates the corresponding angular error distribution after applying a Kalman filter in a CDF chart (average error=12.31°, standard deviation=10.19°). The system captured 11872 independent transponder array readings. The refresh rate was 76.6 Hz.

Based on the experiments, it was determined that non-limiting embodiments of the system and method for tracking a body accurately track the angles of the tested elbow joint. The tests observed a higher refresh rate in the measurements as compared to the knee experiment because the reader was located closer to the elbow than the knee.

To test a shoulder joint, two rectangular arrays of RF transponders (4×2 transponders) were affixed to a cotton sweater. One of the arrays was affixed to the front of the sleeve and the subject was instructed to move the shoulder in an arbitrary path. To retrieve the ground truth, ten reflectors were placed on the subject's chest (five horizontally and five vertically) and three reflectors on the top of the sleeve of the cotton sweater. To compute the ground truth, the ten reflectors were first identified in the same plane and then the relative azimuth and elevation angles of the arm in the plane of the chest were calculated.

Figure 18A:
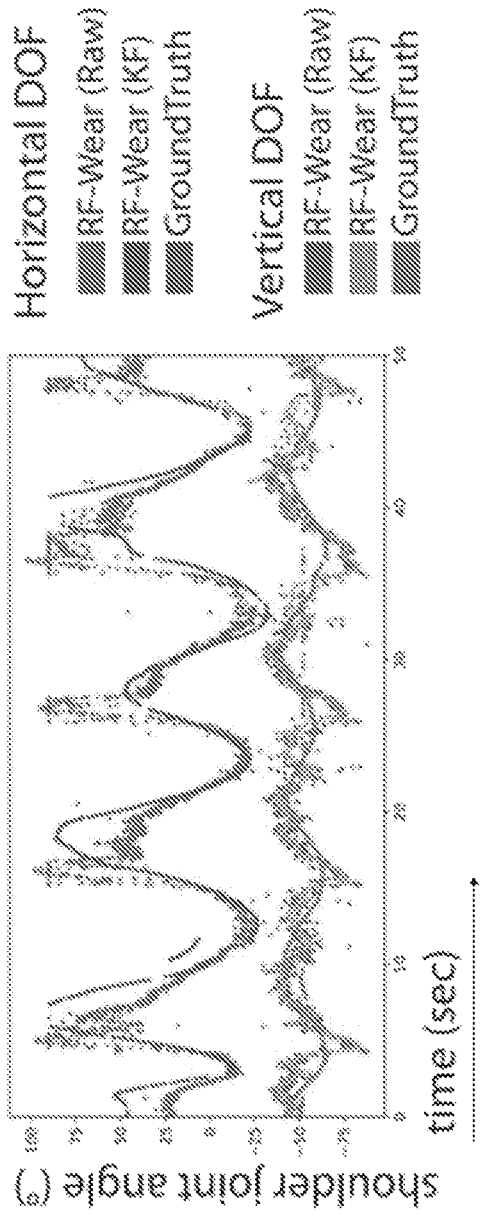
FIGS. 18A-B are charts showing test results for shoulder joint experiments according to non-limiting embodiments.
Figure 18B:
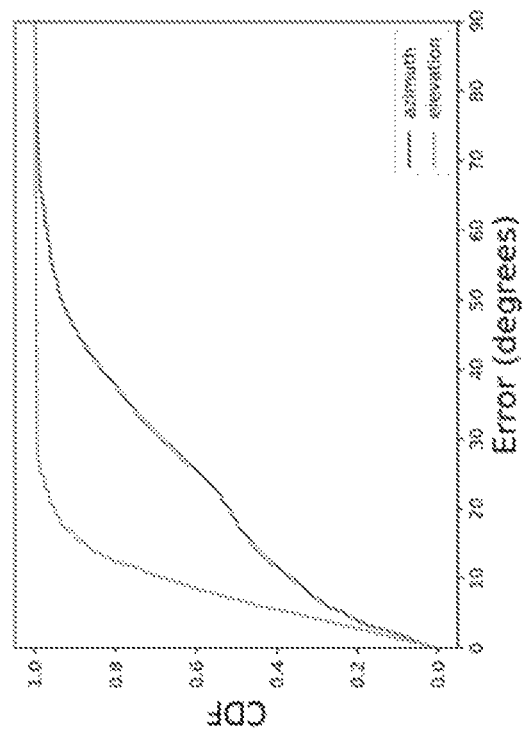

FIGS. 18A and 18B are charts plotting evaluation results for the shoulder experiments. During the test, and as shown in FIG. 18A, 1806 samples were captured in 50 seconds, with 4 peaks among them. The refresh rate was 36.1 Hz. The average error for azimuth and elevation angle was determined to be 21.13° and 7.95°, respectively, with standard deviations of 16.93° and 5.47°. FIG. 18B illustrates the CDF for azimuth and elevation angle after applying Kalman filtering, where the left-most line (with fewer errors until approaching a CDF of 1.0) in the chart represents elevation.

Based on the experiments, a high degree of accuracy was observed in angle-tracking for the shoulder joint having two-degrees-of-freedom. A higher error rate was observed compared to the one-degree-of-freedom joints, likely because arrays of similar dimensions are employed to retrieve two independent angles. It is noted that the error in the polar angle is lower than the error in azimuth angle determination because the polar angle can, at its highest, be 90 degrees while the azimuthal angle varies between 0 and 360 degrees.

Although non-limiting embodiments have been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method for tracking a body comprising a plurality of arrays of radio frequency (RF) transponders arranged thereon, the plurality of arrays comprising a first array of RF transponders arranged on a first portion of the body and a second array of RF transponders arranged on a second portion of the body, the first portion of the body and the second portion of the body connecting at a first joint of the body such that the first array and the second array are separated by the first joint, the method comprising:
communicating, with an antenna of a reader device, at least one activation signal to each RF transponder of the first array and the second array;
receiving, with the antenna, a plurality of response signals from the first array and the second array, the plurality of response signals comprising a response signal for each RF transponder of the first array and the second array;
determining, with at least one processor, a distance between the antenna and each of at least two RF transponders of the first array on the first portion of the body based on at least a first portion of the plurality of response signals;
determining, with at least one processor, a distance between the antenna and each of at least two RF transponders of the second array on the second portion of the body based on at least a second portion of the plurality of response signals;
determining, with at least one processor, a first difference between: the distance between the antenna and a first transponder of the at least two RF transponders of the first array and the distance between the antenna and a second transponder of the at least two RF transponders of the first array;
determining, with at least one processor, a second difference between: the distance between the antenna and a first transponder of the at least two RF transponders of the second array and the distance between the antenna and a second transponder of the at least two RF transponders of the second array; and
determining, with at least one processor, a relative location of the first portion of the body and the second portion of the body based at least partially on the first difference in distances, a distance between the at least two RF transponders of the first array, the second difference in distances, and a distance between the at least two RF transponders of the second array.

2. The method of claim 1, wherein the first difference and the second difference are determined based on phases of the at least a portion of the plurality of response signals.

3. The method of claim 1, wherein the plurality of arrays of RF transponders further comprise a third array of RF transponders arranged on a third portion of the body and a fourth array of RF transponders arranged on a fourth portion of the body, wherein the third portion of the body and the fourth portion of the body connect at a second joint of the body.

4. The method of claim 1, wherein the plurality of arrays of RF transponders are integrated into a fabric material adapted to be worn on the body.

5. The method of claim 1, wherein the reader device is arranged on the body and comprises the at least one processor.

6. The method of claim 1, further comprising determining an angle of the first joint based on the relative location of the first portion of the body with respect to the second portion of the body.

7. The method of claim 1, wherein the at least two RF transponders of the first array are spaced apart by a distance equal to or less than $\lambda/4$, where $\lambda$ is a wavelength of the response signal for each of the at least two RF transponders of the first array.

8. The method of claim 7, wherein each of the at least two RF transponders of the first array are arranged in-line with the first joint.

9. The method of claim 7, wherein the at least two RF transponders of the second array are spaced apart by a distance equal to or less than $\lambda/4$, where $\lambda$ is a wavelength of the response signal for the at least two RF transponders of the second array, and wherein each of the at least two RF transponders of the second array are arranged in-line with the first joint.

10. A system for tracking a body, comprising:
a plurality of arrays of radio frequency (RF) transponders arranged on a body, the plurality of arrays comprising a first array of RF transponders arranged on a first portion of the body and a second array of RF transponders arranged on a second portion of the body, the first portion of the body and the second portion of the body connecting at a first joint of the body such that the first array and the second array are separated by the first joint;
at least one processor programmed and/or configured to:
communicate, with an antenna, at least one activation signal to each RF transponder of the first array and the second array;
receive, with the antenna, a plurality of response signals from the first array and the second array, the plurality of response signals comprising at least one response signal for each RF transponder of the first array and the second array;
determine a distance between the antenna and each of at least two RF transponders of the first array on the first portion of the body based on at least a first portion of the plurality of response signals;
determine a distance between the antenna and each of at least two RF transponders of the second array on the second portion of the body based on at least a second portion of the plurality of response signals;
determine a first difference between: the distance between the antenna and a first transponder of the at least two RF transponders of the first array and the distance between the antenna and a second transponder of the at least two RF transponders of the first array;
determine a second difference between: the distance between the antenna and a first transponder of the at least two RF transponders of the second array and the distance between the antenna and a second transponder of the at least two RF transponders of the second array; and
determine a relative location of the first portion of the body and the second portion of the body based at least partially on the first difference in distances, a distance between the at least two RF transponders of the first array, the second difference in distances, and a distance between the at least two RF transponders of the second array.

11. The system of claim 10, wherein the at least one processor comprises at least one first processor and at least one second processor, the system further comprising a reader device, the reader device including the at least one first processor and the antenna.

12. The system of claim 10, wherein the first difference and the second difference are determined based on phases of response signals received from the at least two RF transponders of the first array.

13. The system of claim 10, wherein the plurality of arrays of RF transponders further comprise a third array of RF transponders arranged on a third portion of the body and a fourth array of RF transponders arranged on a fourth portion of the body, wherein the third portion of the body and the fourth portion of the body connect at a second joint of the body.

14. The system of claim 10, further comprising a fabric material adapted to be worn on the body, wherein the plurality of arrays of RF transponders are integrated into the fabric material.

15. The system of claim 10, wherein the antenna is arranged on the body.

16. The system of claim 10, wherein the at least one processor is further programmed or configured to determine an angle of the first joint based on the relative location of the first portion of the body with respect to the second portion of the body.

17. The system of claim 10, wherein the at least two RF transponders of the first array are spaced apart by a predefined distance and arranged in-line with the first joint, and wherein the at least two RF transponders of the second array are spaced apart by a predefined distance and arranged in-line with the first joint.

18. The system of claim 10, wherein the at least two RF transponders of the first array are spaced apart by a distance equal to or less than $\lambda/4$, where $\lambda$ is a wavelength of the response signal for each of the at least two RF transponders of the first array, and wherein the at least two RF transponders of the second array are spaced apart by a distance equal to or less than $\lambda/4$, where $\lambda$ is a wavelength of the response signal for each of the at least two RF transponders of the second array.

19. A computer program product for tracking a body, wherein a plurality of arrays of radio frequency (RF) transponders are arranged on the body, the plurality of arrays comprising a first array of RF transponders arranged on a first portion of the body and a second array of RF transponders arranged on a second portion of the body, the first portion of the body and the second portion of the body connecting at a first joint of the body such that the first array and the second array are separated by the first joint, the computer program product comprising at least one non-transitory computer-readable medium including program instructions that, when executed by at least one processor, cause the at least one processor to:

communicate, with an antenna, at least one activation signal to each RF transponder of the first array and the second array;

receive, with the antenna, a plurality of response signals from the first array and the second array, the plurality of response signals comprising at least one response signal for each RF transponder of the first array and the second array;

determine a distance between the antenna and each of at least two RF transponders of the first array on the first portion of the body based on at least a first portion of the plurality of response signals;

determine a distance between the antenna and each of at least two RF transponders of the second array on the second portion of the body based on at least a second portion of the plurality of response signals;

determine a first difference between: the distance between the antenna and a first transponder of the at least two RF transponders of the first array and the distance between the antenna and a second transponder of the at least two RF transponders of the first array;

determine a second difference between: the distance between the antenna and a first transponder of the at least two RF transponders of the second array and the distance between the antenna and a second transponder of the at least two RF transponders of the second array; and determine a relative location of the first portion of the body and the second portion of the body based at least partially on the first difference in distances, a distance between the at least two RF transponders of the first array, the second difference in distances, and a distance between the at least two RF transponders of the second array.

20. The computer program product of claim 19, wherein the program instructions, when executed by the at least one processor, further cause the at least one processor to: determine an angle of the first joint based on the relative location of the first portion of the body with respect to the second portion of the body.

21. A system comprising:
a garment comprising:
a first portion of material configured to be worn on a first portion of a body, the first portion of material comprising a first array of radio frequency (RF) transponders arranged in-line with a first joint when the first portion of material is worn on the first portion of the body, the first array comprising at least two RF transponders spaced apart at a first distance such that a first RF transponder of the at least two RF transponders of the first array is farther away from the first joint than a second RF transponder of the at least two RF transponders of the first array when the first portion of material is worn on the first portion of the body; and a second portion of material configured to be worn on a second portion of the body, the second portion of material comprising a second array of RF transponders arranged in-line with the first joint when the first portion of material is worn on the first portion of the body, the second array comprising at least two RF transponders spaced apart at a second distance such that a first RF transponder of the at least two RF transponders of the second array is farther away from the first joint than a second RF transponder of the at least two RF transponders of the second array when the second portion of material is worn on the second portion of the body, wherein the first portion of the body and the second portion of the body connect at the first joint, and wherein the first array and the second array are separated by the first joint when the first portion of material is worn on the first portion of the body and the second portion of material is worn on the second portion of the body; and at least one processor in communication with an antenna, the at least one processor programmed or configured to: (i) receive, with the antenna, a plurality of signals from the first array of RF transponders and the second array of RF transponders, (ii) determine a third distance between the antenna and each of the at least two RF transponders of the first array of RF transponders based on a first portion of the plurality of signals, (iii) determine a fourth distance between the antenna and each of the at least two RF transponders of the second array of RF transponders based on a second portion of the plurality of signals, and (iv) determine a relative location of the first portion of the body and the second portion of the body based at least partially on the first distance, the second distance, the third distance, and the fourth distance.

22. The system of claim 21, wherein the at least two RF transponders of the first array and the at least two RF transponders of the second array are integrated into the first portion of material.

23. The system of claim 22, wherein the at least two RF transponders of the first array and the at least two RF transponders of the second array comprise conductive yarns.

24. The system of claim 22, wherein the first distance and the second distance comprise a predefined distance.

25. The system of claim 21, wherein the garment comprises a shirt, wherein the first portion of material comprises a first portion of a first sleeve, wherein the second portion of material comprises a second portion of the first sleeve, and wherein the first joint comprises an elbow joint.

26. The system of claim 21, wherein the garment comprises a shirt, wherein the first portion of material comprises a first portion of a first sleeve of the shirt, wherein the second portion of material comprises a first portion of a torso section of the shirt, and wherein the first joint comprises a shoulder joint.

27. The system of claim 21, wherein the garment comprises pants and a shirt, wherein the first portion of material comprises a first portion of a torso section of the shirt, wherein the second portion of material comprises a first portion of the pants, and wherein the first joint comprises a hip or waist joint.

28. The system of claim 21, wherein the garment comprises pants, wherein the first portion of material comprises a first portion of a first pant leg, wherein the second portion of material comprises a second portion of the first pant leg, and wherein the first joint comprises a knee joint.

* * * * *